US009988671B2

(12) United States Patent
Saito et al.

(10) Patent No.: US 9,988,671 B2
(45) Date of Patent: *Jun. 5, 2018

(54) DIAGNOSTIC PROBE DETECTION SYSTEM

(71) Applicant: ONE LAMBDA, INC., Canoga Park, CA (US)

(72) Inventors: Katsuyuki Saito, Oak Park, CA (US); Jar-How Lee, Los Angeles, CA (US); Lindley Blair, Los Angeles, CA (US)

(73) Assignee: ONE LAMBDA, INC., Canoga Park, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 13/967,249

(22) Filed: Aug. 14, 2013

(65) Prior Publication Data

US 2013/0330725 A1    Dec. 12, 2013

Related U.S. Application Data

(63) Continuation of application No. 10/253,967, filed on Sep. 24, 2002, now Pat. No. 8,512,953.

(60) Provisional application No. 60/324,421, filed on Sep. 24, 2001.

(51) Int. Cl.
*C12Q 1/68*    (2018.01)

(52) U.S. Cl.
CPC ......... *C12Q 1/6813* (2013.01); *C12Q 1/6827* (2013.01); *C12Q 1/6881* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,835,098 A * | 5/1989 | Orr et al. | 435/6.12 |
| 4,946,773 A | 8/1990 | Maniatis et al. | |
| 5,296,351 A | 3/1994 | Morley et al. | |
| 5,424,413 A | 6/1995 | Hogan et al. | |
| 5,518,884 A | 5/1996 | Spears et al. | |
| 5,589,332 A | 12/1996 | Shih et al. | |
| 5,595,890 A | 1/1997 | Newton et al. | |
| 5,753,439 A | 5/1998 | Smith et al. | |
| 5,780,233 A * | 7/1998 | Guo et al. | 435/6.18 |
| 5,785,835 A | 7/1998 | Saito et al. | |
| 5,854,033 A | 12/1998 | Lizardi | |
| 6,031,091 A | 2/2000 | Arnold, Jr. et al. | |
| 6,194,149 B1 | 2/2001 | Neri et al. | |
| 6,207,379 B1 | 3/2001 | Lee et al. | |
| 6,350,580 B1 | 2/2002 | Sorge | |
| 6,573,051 B2 | 6/2003 | Alsmadi et al. | |
| 8,512,953 B2 * | 8/2013 | Saito et al. | 435/6.12 |

| | | | |
|---|---|---|---|
| 2001/0019825 A1 | 9/2001 | Lee et al. | |
| 2002/0042077 A1 * | 4/2002 | Ellson | 435/6 |
| 2003/0148310 A1 | 8/2003 | Sorge | |

FOREIGN PATENT DOCUMENTS

| | | | |
|---|---|---|---|
| EP | 0237362 A1 | 9/1987 | |
| EP | 0258017 A2 | 3/1988 | |
| EP | 0332435 A2 | 9/1989 | |
| EP | 0450594 A2 | 10/1991 | |
| WO | WO-8706270 A1 | 10/1987 | |
| WO | WO-8810315 A1 | 12/1988 | |
| WO | WO 9723647 A1 * | 7/1997 | ........... C12Q 1/6813 |
| WO | WO 9943853 A1 * | 9/1999 | |
| WO | WO-9943853 A1 | 9/1999 | |
| WO | WO-0079006 A1 | 12/2000 | |

OTHER PUBLICATIONS

Supplemental European Search Report dated Dec. 21, 2004.
Written Opinion corresponding with International Patent Application No. PCT/US02/30238, dated Aug. 26, 2003, IPEA/US, 6 pages.
International Search Report, PCT/US02/30238, United States of America as International Searching Authority, dated Apr. 3, 2003.
Bodmer et al., "Nomenclature for Factors of the HLA System, 1996", *Tissue Antigens*, 49:297-321 (1997).
Sambrook et al, "Molecular Cloning: A Laboratory Manual", *Cold Spring Harbor Press*, 2nd Edition (1989).
The Examination Decision on the Request for Invalidation from the Patent Reexamination of the State Intellectual Property Office of the People's Republic of China, Decision No. 11963, dated Jul. 25, 2008.
Buguwan et al., "A Method for Typing Polymorphism at the HLA-A Locus Using PCR Amplification and Immobilized Oligonucleotide Probes", *Tissue Antigens*, 44:137-147 (1994).
Bunce et al., "Rapid DNA Typing for HLA-C Using Sequence-Specific Primers (PCR-SSP): Identification of Serological and Nonserologically Defined HLA-C Alleles Including Several New Alleles", *Tissue Antigens*, 43:7-17 (1994).
Bunce et al., Phototyping: Comprehensive DNA Typing for HLA-A, B, C, DRB1, DRB2, DRB4, DRB5 & DQB1 by PCR with 144 Primer Mixes Utilizing Sequence-Specific Primers (PCR-SSP), *Tissue Antigens*, 46:355-367 (1995).
Dupont, "Editorial: "Phototyping" for HLA: The Beginning of the End of HLA Typing as We Know It", *Tissue Antigens*, 46:353-354 (1995).

(Continued)

*Primary Examiner* — Suryaprabha Chunduru
(74) *Attorney, Agent, or Firm* — Marshall, Gerstein & Borun LLP

(57) ABSTRACT

The invention provides methods for detecting target nucleic acid sequences with diagnostic probes including first and second probe regions that are substantially complementary to first and second target regions respectively on a target nucleic acid strand wherein the first probe region is located 5' to the second probe region. The first probe region is substantially complementary to the first target region, on the target nucleic acid strand, which also includes a second target region, wherein when the first target region is contiguous with the second target region on the target nucleic acid strand, then the first and second probe regions on the diagnostic probe are separated by a spacer region of nucleic acid.

14 Claims, 5 Drawing Sheets

(56) References Cited

OTHER PUBLICATIONS

Gentalen et al., "A Novel Method for Determining Linkage Between DNA Sequences: Hybridization to Paired Probe Arrays", *Nucleic Acids Research*, 27:1485-1491 (1999).
Horton et al., "Gene Splicing by Overlap Extension: Tailor-Made Genes Using the Polymerase Chain Reaction", *BioTechniques*, vol. 8, No. 5, 528 (1990).
Lizardi et al., "Exponential Amplification of Recombinant-RNA Hybridization Probes", *Biotechnology*, 6:1197-1202 (1988).
Olerup et al., "HLA-DQB1 and -DQA1 Typing by PCR Amplification with Sequence-Specific Primers (PCR-SSP) in 2 Hours", *Tissue Antigens*, 41:119-134 (1993).
Senanayake et al., "Precise Large Deletions by the PCR-Based Overlap Extension Method", *Molecular Biology*, 4:13-15 (1995).
Zoller et al., "Oligonucleotide-Directed Mutagenesis: A Simple Method Using Two Oligonucleotide Primers and a Single-Stranded DNA Template", *Methods in Enzymology*, 154:329-350 (1987).

\* cited by examiner

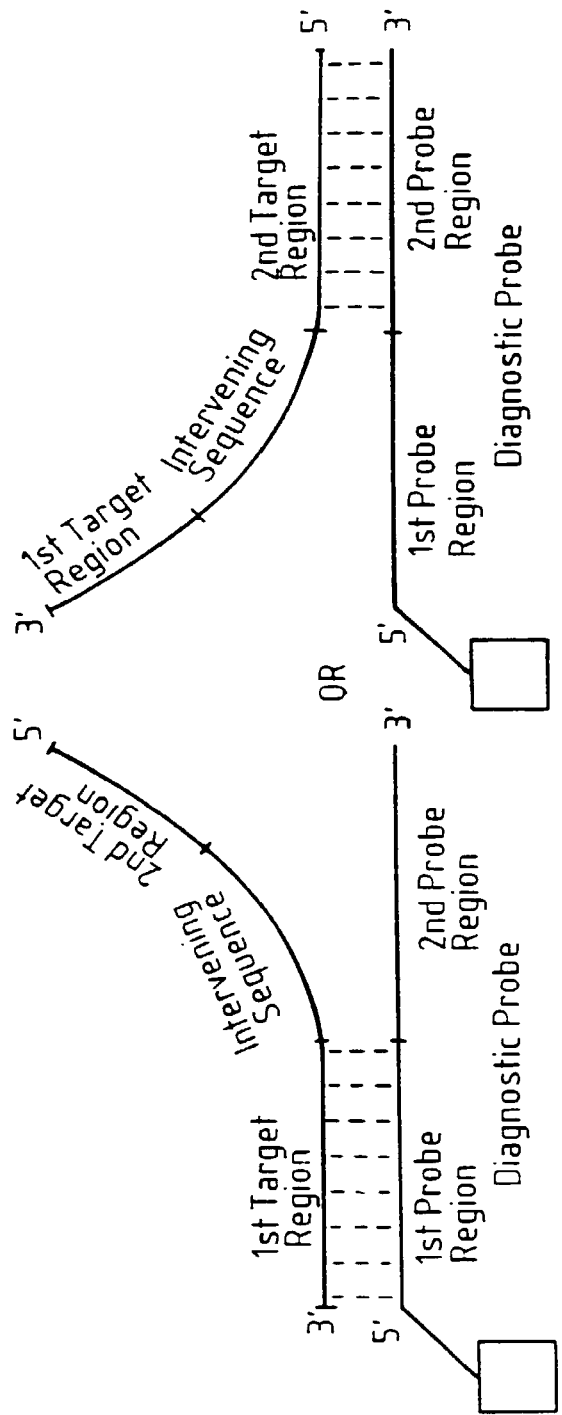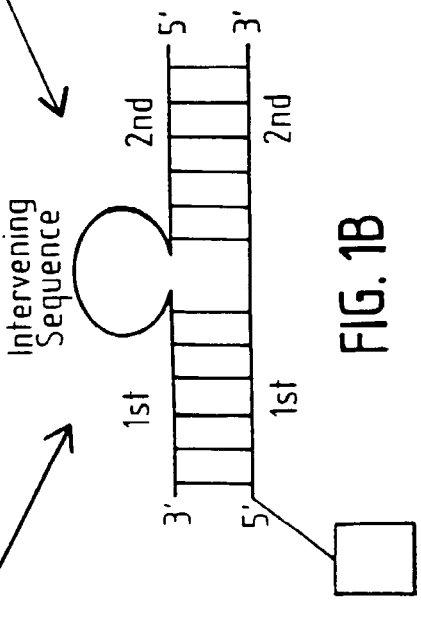
FIG. 1A  FIG. 1A'
FIG. 1B

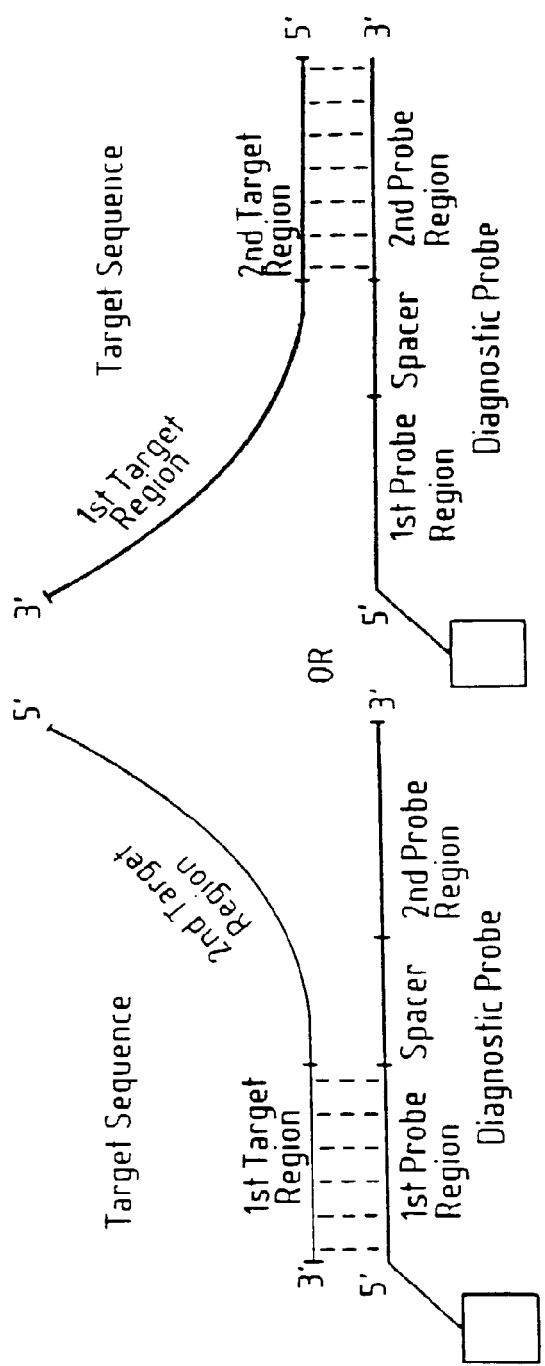
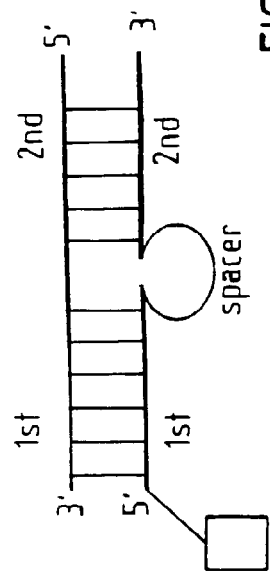
FIG. 2A    FIG. 2A'
FIG. 2B

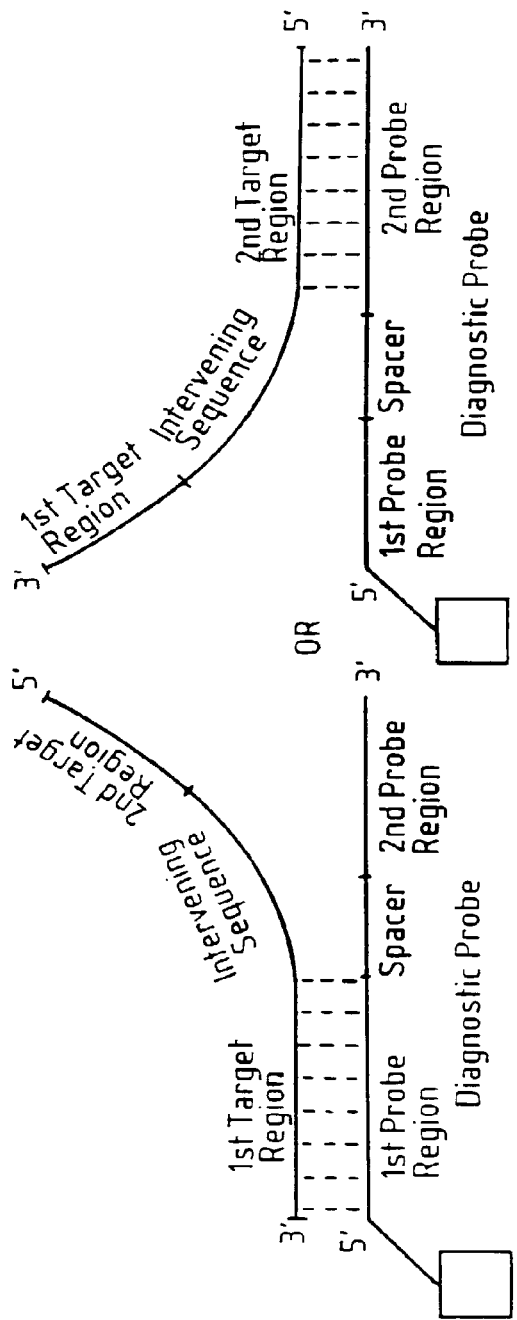
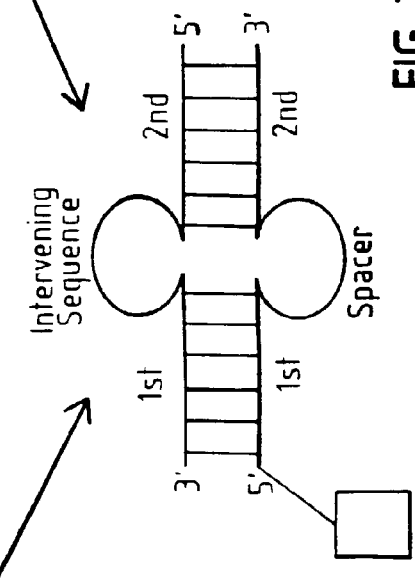
FIG. 3A  FIG. 3A'
FIG. 3B

To FIG. 4C

SEQUENCE LISTING

```
<160> NUMBER OF SEQ ID NOS: 53

<210> SEQ ID NO 1
<211> LENGTH: 21
<212> TYPE: DNA
<213> ORGANISM: Homo sapiens
<220> FEATURE:
<221> NAME/KEY: misc_feature
<223> OTHER INFORMATION: Allele DRB*0101

<400> SEQUENCE: 1
cggcctgatg ccgagtactg g                                              21

<210> SEQ ID NO 2
<211> LENGTH: 21
<212> TYPE: DNA
<213> ORGANISM: Homo sapiens
<220> FEATURE:
<221> NAME/KEY: misc_feature
<223> OTHER INFORMATION: Allele DRB*0101

<400> SEQUENCE: 2
gagcagaggc gggccgcggt g                                              21

<210> SEQ ID NO 3
<211> LENGTH: 21
<212> TYPE: DNA
<213> ORGANISM: Homo sapiens
<220> FEATURE:
<221> NAME/KEY: misc_feature
<223> OTHER INFORMATION: Allele DRB*0415, Alleles DRB1*11011/01
      2/041/042/05/0 6/081/082 /09/1 0/121/122/13/ 15/18/19/22/24/
      26-30/34/37/39

<400> SEQUENCE: 3
cggcctgatg aggagtactg g                                              21

<210> SEQ ID NO 4
<211> LENGTH: 21
<212> TYPE: DNA
<213> ORGANISM: Homo sapiens
```

```
<220> FEATURE:
<221> NAME/KEY: misc_feature
<223> OTHER INFORMATION: Allele DRB1*0308, DRB1*1107

<400> SEQUENCE: 4
gagcagaagc ggggccgggt g                                              21

<210> SEQ ID NO 5
<211> LENGTH: 18
<212> TYPE: DNA
<213> ORGANISM: Artificial sequence
<220> FEATURE:
<223> OTHER INFORMATION: Conventional probe, OLR4040

<400> SEQUENCE: 5
gcctgatgag gagtactg                                                  18

<210> SEQ ID NO 6
<211> LENGTH: 15
<212> TYPE: DNA
<213> ORGANISM: Artificial sequence
<220> FEATURE:
<223> OTHER INFORMATION: Conventional probe, OLR4040

<400> SEQUENCE: 6
aagcggggcc gggtg                                                     15

<210> SEQ ID NO 7
<211> LENGTH: 31
<212> TYPE: DNA
<213> ORGANISM: Artificial sequence
<220> FEATURE:
<223> OTHER INFORMATION: Gap probe, OLR4431-3

<400> SEQUENCE: 7
ctgatgagga gtacttttag cagaagcggg g                                   31

<210> SEQ ID NO 8
<211> LENGTH: 9
<212> TYPE: DNA
<213> ORGANISM: Homo sapiens

<400> SEQUENCE: 8 aagcggggc                                                             9

<210> SEQ ID NO 9
<211> LENGTH: 17
<212> TYPE: DNA
<213> ORGANISM: Artificial sequence
<220> FEATURE:
<223> OTHER INFORMATION: Positive control probe

<400> SEQUENCE: 9
ggaacagcca gaaggac                                                   17

<210> SEQ ID NO 10
<211> LENGTH: 14
<212> TYPE: DNA
<213> ORGANISM: Artificial sequence
<220> FEATURE:
<223> OTHER INFORMATION: Probe region

<400> SEQUENCE: 10
ctgatgagga gtac                                                      14
```

```
<210> SEQ ID NO 11
<211> LENGTH: 13
<212> TYPE: DNA
<213> ORGANISM: Artificial sequence
<220> FEATURE:
<223> OTHER INFORMATION: Probe region

<400> SEQUENCE: 11
agcagaagcg ggg                                                          13

<210> SEQ ID NO 12
<211> LENGTH: 27
<212> TYPE: DNA
<213> ORGANISM: Homo sapiens
<220> FEATURE:
<221> NAME/KEY: misc_feature
<223> OTHER INFORMATION: Allele A*0101

<400> SEQUENCE: 12
gaccaggaga cacggaatat gaaggcc                                           27

<210> SEQ ID NO 13
<211> LENGTH: 25
<212> TYPE: DNA
<213> ORGANISM: Homo sapiens
<220> FEATURE:
<221> NAME/KEY: misc_feature
<223> OTHER INFORMATION: Allele A*0101

<400> SEQUENCE: 13
cctggggacc ctgcgcggct actac                                             25

<210> SEQ ID NO 14
<211> LENGTH: 27
<212> TYPE: DNA
<213> ORGANISM: Homo sapiens
<220> FEATURE:
<221> NAME/KEY: misc_feature
<223> OTHER INFORMATION: Allele A*2424, A*2501-2504

<400> SEQUENCE: 14
gaccggaaca cacggaatgt gaaggcc                                           27

<210> SEQ ID NO 15
<211> LENGTH: 27
<212> TYPE: DNA
<213> ORGANISM: Homo sapiens
<220> FEATURE:
<221> NAME/KEY: misc_feature
<223> OTHER INFORMATION: Allele A*0301

<400> SEQUENCE: 15
gaccaggaga cacggaatgt gaaggcc                                           27

<210> SEQ ID NO 16
<211> LENGTH: 25
<212> TYPE: DNA
<213> ORGANISM: Homo sapiens
<220> FEATURE:
<221> NAME/KEY: misc_feature
<223> OTHER INFORMATION: Allele A*2424, A82501~04

<400> SEQUENCE: 16
cctgcggatc gcgctccgct actac                                             25
```

-continued

<210> SEQ ID NO 17
<211> LENGTH: 30
<212> TYPE: DNA
<213> ORGANISM: Artificial sequence
<220> FEATURE:
<223> OTHER INFORMATION: Gap Probe, A*68012

<400> SEQUENCE: 17
cggaacacac ggattttgga tcgcgctccg                                            30

<210> SEQ ID NO 18
<211> LENGTH: 20
<212> TYPE: DNA
<213> ORGANISM: Artificial sequence
<220> FEATURE:
<223> OTHER INFORMATION: Probe, A104-11

<400> SEQUENCE: 18
ggaacacacg gaatgtgaag                                                      20

<210> SEQ ID NO 19
<211> LENGTH: 25
<212> TYPE: DNA
<213> ORGANISM: Artificial sequence
<220> FEATURE:
<223> OTHER INFORMATION: Probe, A150-19

<400> SEQUENCE: 19
cctgcggatc gcgctccgct actac                                                25

<210> SEQ ID NO 20
<211> LENGTH: 20
<212> TYPE: DNA
<213> ORGANISM: Artificial sequence
<220> FEATURE:
<223> OTHER INFORMATION: Positive control probe

<400> SEQUENCE: 20
gctactacaa ccagagcgag                                                      20

<210> SEQ ID NO 21
<211> LENGTH: 21
<212> TYPE: DNA
<213> ORGANISM: Homo sapiens
<220> FEATURE:
<221> NAME/KEY: misc_feature
<223> OTHER INFORMATION: Allele A*0101

<400> SEQUENCE: 21
acacggaata tgaaggccca c                                                    21

<210> SEQ ID NO 22
<211> LENGTH: 21
<212> TYPE: DNA
<213> ORGANISM: Homo sapiens
<220> FEATURE:
<221> NAME/KEY: misc_feature
<223> OTHER INFORMATION: Allele A*0101

<400> SEQUENCE: 22
aacctgggga ccctgcgcgg c                                                    21

<210> SEQ ID NO 23
<211> LENGTH: 21
<212> TYPE: DNA
<213> ORGANISM: Homo sapiens

```
<220> FEATURE:
<221> NAME/KEY: misc_feature
<223> OTHER INFORMATION: Allele B*1523, B*3801

<400> SEQUENCE: 23
acacagatct gcaagaccaa c                                              21

<210> SEQ ID NO 24
<211> LENGTH: 21
<212> TYPE: DNA
<213> ORGANISM: Homo sapiens
<220> FEATURE:
<221> NAME/KEY: misc_feature
<223> OTHER INFORMATION: Allele B*1523, B*3801

<400> SEQUENCE: 24
aacctgcgga tcgcgctccg c                                              21

<210> SEQ ID NO 25
<211> LENGTH: 21
<212> TYPE: DNA
<213> ORGANISM: Homo sapiens
<220> FEATURE:
<221> NAME/KEY: misc_feature
<223> OTHER INFORMATION: Allele B*1401, B*1521, B*3901

<400> SEQUENCE: 25
agcctgcgga acctgcgcgg c                                              21

<210> SEQ ID NO 26
<211> LENGTH: 21
<212> TYPE: DNA
<213> ORGANISM: Homo sapiens
<220> FEATURE:
<221> NAME/KEY: misc_feature
<223> OTHER INFORMATION: Allele B*5501

<400> SEQUENCE: 26
acacagatct tcaagaccaa c                                              21

<210> SEQ ID NO 27
<211> LENGTH: 21
<212> TYPE: DNA
<213> ORGANISM: Homo sapiens
<220> FEATURE:
<221> NAME/KEY: misc_feature
<223> OTHER INFORMATION: Allele B*5501

<400> SEQUENCE: 27
acacagatct acaaggccca g                                              21

<210> SEQ ID NO 28
<211> LENGTH: 21
<212> TYPE: DNA
<213> ORGANISM: Homo sapiens
<220> FEATURE:
<221> NAME/KEY: misc_feature
<223> OTHER INFORMATION: Allele B*4601

<400> SEQUENCE: 28
acacagaagt acaagcgcca g                                              21

<210> SEQ ID NO 29
<211> LENGTH: 31
<212> TYPE: DNA
<213> ORGANISM: Artificial sequence
```

```
<220> FEATURE:
<223> OTHER INFORMATION: Gap probe, B204

<400> SEQUENCE: 29
acacagatct gcaagtttgg atcgcgctcc g                                31

<210> SEQ ID NO 30
<211> LENGTH: 18
<212> TYPE: DNA
<213> ORGANISM: Artificial sequence
<220> FEATURE:
<223> OTHER INFORMATION: Probe, B153

<400> SEQUENCE: 30
acctgcggat cgcgctcc                                               18

<210> SEQ ID NO 31
<211> LENGTH: 18
<212> TYPE: DNA
<213> ORGANISM: Artificial sequence
<220> FEATURE:
<223> OTHER INFORMATION: Probe B106

<400> SEQUENCE: 31
acacagatct gcaagacc                                               18

<210> SEQ ID NO 32
<211> LENGTH: 19
<212> TYPE: DNA
<213> ORGANISM: Artificial sequence
<220> FEATURE:
<223> OTHER INFORMATION: Prositive control probe

<400> SEQUENCE: 32
gctactacaa ccagagcga                                              19

<210> SEQ ID NO 33
<211> LENGTH: 24
<212> TYPE: DNA
<213> ORGANISM: Homo sapiens
<220> FEATURE:
<221> NAME/KEY: misc_feature
<223> OTHER INFORMATION: Allele DQB1*05011

<400> SEQUENCE: 33
ccgcaggggc ggcctgttgc cgag                                        24

<210> SEQ ID NO 34
<211> LENGTH: 21
<212> TYPE: DNA
<213> ORGANISM: Homo sapiens
<220> FEATURE:
<221> NAME/KEY: misc_feature
<223> OTHER INFORMATION: Allele DQB1*05011

<400> SEQUENCE: 34
ctggaggggg cccgggcgtc g                                           21

<210> SEQ ID NO 35
<211> LENGTH: 24
<212> TYPE: DNA
<213> ORGANISM: Homo sapiens
<220> FEATURE:
<221> NAME/KEY: misc_feature
<223> OTHER INFORMATION: Allele DQB1*06011
```

<400> SEQUENCE: 35
ccgcaggggc ggcctgacgc cgag                                    24

<210> SEQ ID NO 36
<211> LENGTH: 21
<212> TYPE: DNA
<213> ORGANISM: Homo sapiens
<220> FEATURE:
<221> NAME/KEY: misc_feature
<223> OTHER INFORMATION: Allele DQB1*06011

<400> SEQUENCE: 36
ctggagagga cccgagcgga g                                       21

<210> SEQ ID NO 37
<211> LENGTH: 29
<212> TYPE: DNA
<213> ORGANISM: Artificial sequence
<220> FEATURE:
<223> OTHER INFORMATION: Gap probe, DQ54G-3

<400> SEQUENCE: 37
ggcctgacgc cgattttctg gagggggcc                               29

<210> SEQ ID NO 38
<211> LENGTH: 18
<212> TYPE: DNA
<213> ORGANISM: Artificial sequence
<220> FEATURE:
<223> OTHER INFORMATION: Probe, DQ25-8

<400> SEQUENCE: 38 gcagggcgg cctgacgc                                            18

<210> SEQ ID NO 39
<211> LENGTH: 18
<212> TYPE: DNA
<213> ORGANISM: Artificial sequence
<220> FEATURE:
<223> OTHER INFORMATION: Probe, DQ33

<400> SEQUENCE: 39 tggaggggc ccgggcgt                                            18

<210> SEQ ID NO 40
<211> LENGTH: 21
<212> TYPE: DNA
<213> ORGANISM: Artificial sequence
<220> FEATURE:
<223> OTHER INFORMATION: Positive control probe

<400> SEQUENCE: 40
gtcccgttgg tgaagtagca c                                       21

<210> SEQ ID NO 41
<211> LENGTH: 21
<212> TYPE: DNA
<213> ORGANISM: Artificial sequence
<220> FEATURE:
<223> OTHER INFORMATION: Positive control probe

<400> SEQUENCE: 41
gtcccattgg tgaagtagca c                                       21

```
<210> SEQ ID NO 42
<211> LENGTH: 18
<212> TYPE: DNA
<213> ORGANISM: Homo sapiens
<220> FEATURE:
<221> NAME/KEY: misc_feature
<223> OTHER INFORMATION: Allele OLR-4611

<400> SEQUENCE: 42
ctgatgagga gtactttt                                                 18

<210> SEQ ID NO 43
<211> LENGTH: 14
<212> TYPE: DNA
<213> ORGANISM: Artificial sequence
<220> FEATURE:
<223> OTHER INFORMATION: Probe, OLR-4612

<400> SEQUENCE: 43
ctgatgagga gtac                                                     14

<210> SEQ ID NO 44
<211> LENGTH: 13
<212> TYPE: DNA
<213> ORGANISM: Artificial sequence
<220> FEATURE:
<223> OTHER INFORMATION: Probe, OLR-4613

<400> SEQUENCE: 44
agcagaagcg ggg                                                      13

<210> SEQ ID NO 45
<211> LENGTH: 12
<212> TYPE: DNA
<213> ORGANISM: Artificial sequence
<220> FEATURE:
<223> OTHER INFORMATION: Probe, OLR-4614

<400> SEQUENCE: 45
agcagaagcg gg                                                       12

<210> SEQ ID NO 46
<211> LENGTH: 17
<212> TYPE: DNA
<213> ORGANISM: Artificial sequence
<220> FEATURE:
<223> OTHER INFORMATION: Positive control probe

<400> SEQUENCE: 46
ggaacagcca gaaggac                                                  17

<210> SEQ ID NO 47
<211> LENGTH: 27
<212> TYPE: DNA
<213> ORGANISM: Homo sapiens
<220> FEATURE:
<221> NAME/KEY: misc_feature
<223> OTHER INFORMATION: Reference sequence

<400> SEQUENCE: 47
ttgtggcagc ttaagtttga atgtcat                                       27

<210> SEQ ID NO 48
<211> LENGTH: 21
<212> TYPE: DNA
<213> ORGANISM: Homo sapiens
```

```
<220> FEATURE:
<221> NAME/KEY: misc_feature
<223> OTHER INFORMATION: Reference sequence

<400> SEQUENCE: 48
ctcctggagc agaggcgggc c                                              21

<210> SEQ ID NO 49
<211> LENGTH: 27
<212> TYPE: DNA
<213> ORGANISM: Homo sapiens
<220> FEATURE:
<221> NAME/KEY: misc_feature
<223> OTHER INFORMATION: Alleles DRB1*1501 and DRB1*1502

<400> SEQUENCE: 49
ctgtggcagc ctaagaggga gtgtcat                                        27

<210> SEQ ID NO 50
<211> LENGTH: 21
<212> TYPE: DNA
<213> ORGANISM: Homo sapiens
<220> FEATURE:
<221> NAME/KEY: misc_feature
<223> OTHER INFORMATION: Alleles DRB1*1501 and DRB1*1502

<400> SEQUENCE: 50
atcctggagc aggcgcgggc c                                              21

<210> SEQ ID NO 51
<211> LENGTH: 21
<212> TYPE: DNA
<213> ORGANISM: Homo sapiens
<220> FEATURE:
<221> NAME/KEY: misc_feature
<223> OTHER INFORMATION: Allele DRB1*16011

<400> SEQUENCE: 51
ttcctggaag acaggcgcgc c                                              21

<210> SEQ ID NO 52
<211> LENGTH: 21
<212> TYPE: DNA
<213> ORGANISM: Homo sapiens
<220> FEATURE:
<221> NAME/KEY: misc_feature
<223> OTHER INFORMATION: Allele DRB1*16021

<400> SEQUENCE: 52
ctcctggaag acaggcgcgc c                                              21

<210> SEQ ID NO 53
<211> LENGTH: 27
<212> TYPE: DNA
<213> ORGANISM: Artificial sequence
<220> FEATURE:
<223> OTHER INFORMATION: Gap probe, OLR-4029-6

<400> SEQUENCE: 53
cctaagaggg agtgtctgga agacagg                                        27
```

DIAGNOSTIC PROBE DETECTION SYSTEM

This application is a continuation of U.S. application Ser. No. 10/253,967, filed Sep. 24, 2002, which claims priority benefit of U.S. Provisional Application No. 60/324,421, filed Sep. 24, 2001, incorporated herein by reference in its entirety.

BACKGROUND OF THE INVENTION

The present invention relates to methods for the detection of the presence or absence of nucleic acid sequences that are characteristic of pathogens and the like as well as of gene variations and mutations including those relating to the human leukocyte antigen (HLA), which is of interest in the field of human transplantation. Variations and mutations relating to T-cell receptor (TCR) gene sequences are also of interest.

The HLA locus is highly polymorphic in nature. As disclosed in the Nomenclature for Factors of the HLA System 2000 (Hum. Immunol. 2001 April; 62(4):419-68), there are 124 HLA-A alleles, 258 HLA-B alleles, 74 HLA-C alleles, 221 HLA-DRB1 alleles, 19 DRB3 alleles, 89 DRB4 alleles, 14 DRBS alleles, 19 DQA1 alleles and 39 DQB1 alleles, with new alleles being discovered continuously. As testament to this rapid progress, a July 2002 update by the WHO nomenclature Committee for Factors of the HLA System showed there are 250 HLA-A alleles, 488 HLA-B alleles, 118 HLA-C alleles, 312 HLA-DRB1 alleles, 38 HLA-DRB3 alleles, 12 HLA-DRB4 alleles, 25 HLA-DRBS alleles, 22 DQA1 alleles, 53 DQB1 alleles, 20 DPA1 and 99 DPB1 alleles.

All HLA-A, -B, and -C alleles have similar sequences. The same holds for DRB1, DRB3, DRB4 and DRBS sequences. Because of these similarities, very often when a primer pair is used in the practice of polymerase chain reaction sequence-specific priming (PCR-SSP), two or more alleles will be amplified, or in a diagnostic sequence-specific oligonucleotide-probe detection (SSO) system, two or more alleles will hybridize. Therefore, for each allele to have a unique PCR-SSP or detection-SSO pattern, many pairs of primers or probes must be used. Further, the use of diagnostic hybridization SSO probes in HLA typing is confounded by the high levels of homology shared by the HLA alleles. Thus, many prior art typing methods such as those of Bugawan et al., Tissue Antigens (1994)44:137-147, lack the accuracy desired for HLA typing and other applications.

PCR can be used to characterize the sequence on the target DNA template. If amplification occurs, the template DNA contains the same sequences as the primers used. If no amplification occurs, the sequences on the template DNA are different from the primer sequences. Newton et al., U.S. Pat. No. 5,595,890 disclose PCR diagnostic methods for typing, including molecular typing of HLA using PCR-SSP. According to this method, an unknown allele is assigned based on the pattern of positive or negative reactions from multiple rounds of PCR. The methods disclosed by Newton are limited in their effectiveness for HLA typing, however, due to the high degree of polymorphism in HLA as described above. As a consequence two primers, each with specific sequences, frequently amplify many HLA alleles, thus increasing the number of PCR amplifications required in order to assign an unknown allele. For similar reasons, multiple diagnostic probes are required for correct typing of HLA in non-PCR contexts. PCR requires a pair of primers flanking the region on the DNA template for that region to be amplified. The ability of a primer to anneal to the desired sequence depends on the length of the primer and the annealing temperature set in the PCR thermocycling program. The longer the primer, the higher the annealing temperature it needs to achieve specific amplification of a DNA sequence. PCR-SSP uses a balance between primer length and annealing temperature to achieve the specificity of the primer-directed sequence amplification.

In the clinical use of PCR-SSP systems for HLA typing, there had existed a need to use a limited number of PCR reactions to achieve as much resolution as possible whereby the number of alleles amplified by a pair of primers would be reduced (i.e., the specificity of the primers or probes would be increased). Of interest to the present invention is the disclosure of co-owned U.S. Pat. No. 6,207,379, the disclosure of which is hereby incorporated by reference, which teaches the use of diagnostic PCR primers that are characterized by non-contiguous (gap) sequences for obtaining greater discrimination between related alleles in HLA typing. In an alternative embodiment, U.S. Pat. No. 6,207,379 teaches use of diagnostic primers that hybridize to non-contiguous sequences in a target nucleic acid and amplify that target by polymerase-mediated primer extension. Despite the success of the methods of U.S. Pat. No. 6,207,379 in carrying out more specific amplification of the target HLA sequences there still remains a desire for improved methods for detection of HLA sequences in both PCR and non-PCR contexts.

The PCR invention described in U.S. Pat. No. 6,207,379 addressed the need in the art for improved methods of PCR-SSP-based molecular typing whereby the specificity of the typing can be increased so as to reduce the number of PCR reactions required for each typing. However, there still exists a need in the art for methods to probe for specific sequences in non-PCR contexts. For reasons of basic thermodynamics, probes and templates, including those with a perfect match, are in state of equilibrium between the hybridized and non-hybridized state. A probe that is at one moment attached to its target template, at another moment may not be. The polymerase in PCR plays a critical role by locking a primer in place through elongation. In non-PCR contexts, the critical factor—the polymerase (and the subsequent elongation)—is lacking, and long-term stability of the hybridized duplex of a short probe to a target would not necessarily be expected. For these reasons it is generally considered necessary for hybridization probes to be longer than corresponding extension primers in order to assure stable duplex formation.

Also of interest to the present invention is the disclosure of Gentalen et al., Nucleic Acids Research Vo. 27, No. 6, pp 1485-1491 (1999), which teaches a method for determining physical linkage between two loci on a DNA strand by means of a high-density oligonucleotide array having more than one oligonucleotide probe at the same address on the oligonucleotide array. According to Gentalen, cooperative hybridization is capable of distinguishing between physically linked and unlinked target sequences.

Accordingly, there remains a need for improved hybridization-based detection systems that are capable of reliably detecting specific targets in highly polymorphic contexts including HLA typing and identification of T-cell receptor (TCR) gene sequences.

SUMMARY OF THE INVENTION

The present invention relates to improved methods for detecting sample/target nucleic acid sequences and in particular for the detection of nucleic acids encoding human leukocyte antigens (HLA) and detection of T-cell receptor (TCR) gene sequences whereby the specificity of diagnostic probes is increased such that at least one probe is capable of recognizing two or more regions on the target and is preferably capable of doing so without increasing the annealing temperature of the probe to the sample/target nucleic acid sequence. The increased specificity of the probe set reduces the number of alleles detected, thus increasing the resolution of the method, and does so at lower cost.

Specifically, the invention provides a method for detecting the presence of a target nucleic acid sequence on a sample nucleic acid strand comprising the steps of: contacting a sample suspected of containing the target nucleic acid sequence with a diagnostic probe under hybridizing conditions. The nucleotide sequence of this diagnostic probe comprises both a first probe region at its 5'-end that is substantially complementary to a first target region characteristic of said target nucleic acid sequence, and a second probe region located 3' to said first probe region. The second probe region is substantially complementary to a second target region characteristic of said target nucleic acid sequence on the target nucleic acid strand. When the first target region is contiguous with the second target region on the target nucleic acid strand then the first and second probe regions on the diagnostic probe are separated by a spacer region of nucleic acid. When the first and second probe regions on the diagnostic probe are contiguous, then there exists an intervening sequence between the first and second target regions on the target nucleic acid strand. For the selected hybridization conditions the lengths of the first and second probe regions are such that the diagnostic probe is stably hybridized to the target nucleic acid strand to form a detectable probe:target hybrid when both the first probe region is substantially complementary to the first target region and the second probe region is substantially complementary to the second target region. However, under the selected hybridization conditions the diagnostic probe is not stably hybridized to the target nucleic acid strand to form a probe:target hybrid detectable above a threshold indicative of stable hybridization when either the first probe region or the second probe region is not substantially complementary to the first and second target regions, respectively. The presence or absence of the stable probe:target hybrid is then detected as an indication of the presence or absence of the target nucleic acid sequence in the sample.

According to practice of the invention, the target nucleic acid and the nucleic acid probes of the invention can be DNA, RNA or synthetic DNA molecules having modified backbones such as with sulfate or peptide bonds rather than phosphate bonds.

While it is recognized that detectable signals can be produced in the absence of stable hybridization, those of skill in the art recognize that the presence or absence of stable hybridization can be determined by a comparison of signals produced by both negative and positive controls and that signal thresholds can be determined that allow making distinctions between stable and unstable (including transient) hybridization indicative of the presence or absence of a target nucleic acid sequence in a sample. According to one method, the threshold for designating a "positive" reaction can be selected as the mid-point between the lowest value for positive control samples and the highest value for negative control samples under a selected set of conditions.

According to a preferred aspect of the present invention, the first probe region and the second probe region are exactly complementary to the first and second target regions respectively, but they need not be. According to a preferred aspect of the present invention, the sample/target nucleic acid strand or strands are derived from a human subject, but they need not be.

While the first probe region and second probe region can be contiguous on the diagnostic probes of the invention, they need not be. Thus, according to one preferred embodiment of the invention, the first probe region and the second probe region may be separated by a spacer region of nucleic acid sequence that is not complementary to the sequence of the target nucleic acid strand between the first target region and the second target region sequences, i.e. the "intervening sequence". Specifically, the spacer region is selected so as to provide a discontinuity in the complementarity of the nucleotide sequences of the first probe region and the second probe region of the diagnostic probe such that stable hybridization of the target nucleic acid sequence will not occur unless the first probe region and the second probe region are substantially complementary to the first and second target regions, respectively. According to a further embodiment of the method of the invention, the invention may also be practiced where there exists a spacer region between the first and second probe regions and there also exists an intervening sequence between the first and second target regions on said target nucleic acid.

The spacer region between the probe regions on the probe is generally more than one nucleotide but less than 350 nucleotides in length with lengths of from 1 to 30 nucleotides being preferred and with 3 to 10 nucleotides being particularly preferred. In most circumstances, the spacer region need be no more than 10 or 20 nucleotide bases in length. In contrast, the intervening sequence between target regions on the target nucleic acid can be from 1 to 500 or more bases in length with less than 350 (1-350 bases) nucleotides being preferred. Nevertheless, the length of the spacer region, as well as the length of intervening sequence between the target regions on the target nucleic acid strand, should not be so long that cooperative binding of probe regions to their respective target regions would be prevented. Moreover, the lengths of the probe and target regions should not be so long that either probe region is able to hybridize independently to its target region by virtue of increased length (and therefore increased annealing temperature) without requiring prior transient hybridization of the other probe region to its target region. Only when both probe regions stably hybridize to their respective target regions will a signal above a threshold be indicative of the presence of the target nucleic acid be produced.

In another aspect, this invention teaches a method for detecting the presence of two or more target nucleic acid sequences on two or more sample nucleic acid strands comprising the steps of contacting a sample suspected of containing said target nucleic acid sequences with a diagnostic probe under hybridizing conditions. The first target nucleic acid sequence has a first target region and a first complementary target zone. The second nucleic acid sequence has a second target region and a second complementary target zone. The nucleotide sequence of said diagnostic probe comprises (1) a first probe region that is substantially complementary to a first target region characteristic of said first target nucleic acid sequence, and (2) a second probe region, where the second probe region is substantially complementary to a second target region characteristic of said second target nucleic acid sequence. For the selected hybridization conditions, when the first and second probe regions are such that the diagnostic probe is stably hybridized to the target nucleic acid strand to form a detectable probe:target hybrid when the first complementary target zone is substantially complementary to the second complementary target zone, the first probe region is substantially complementary to the first target region, and the second probe region is substantially complementary to the second target region. However, for the selected hybridization conditions, when the diagnostic probe is not stably hybridized to the target nucleic acid strand to form a probe:target hybrid detectable above a threshold indicative of stable hybridization when either the first complementary target zone is not substantially complementary to the second complementary target zone, or the first probe region is not substantially complementary to the first target region or the second probe region is not substantially complementary to the second target region. The presence or absence of the stable probe:target hybrid is then detected as an indication of the presence or absence of the target nucleic acid sequence in the sample.

In some embodiments, the first and second probe regions on the diagnostic probe are separated by a spacer region of nucleic acid sequence. In some embodiments, either the first target region and the first complementary target zone are separated by a first non-complementary zone, or a second target region and a second complementary target zone are separated by a second non-complementary zone.

In some embodiments comprising complementary target zones, the first target region and the first complementary target zone may be separated by a first non-complementary zone, or a second target region and a second complementary target zone may be separated by a second non-complementary zone. In such embodiments, the first and second non-complementary zones are not substantially complementary to each other and not substantially complementary to the spacer region.

In those embodiments where a spacer is present, the spacer is generally more than one nucleotide but less than 350 nucleotides in length with lengths from 1 to 30 nucleotides (bases) long being preferred and with 3 to 10 nucleotides (bases) being particular preferred. In most circumstances, the spacer region need be no more than 10 or 20 nucleotide bases in length. In contrast, the non-complementary zones (NCZ) between target regions and complementary target zones (CTZ) on the target nucleic acids can be from 1 to 500 or more bases in length with less than 350 (0-350 bases) nucleotides being preferred. Nevertheless, the length of the spacer region, as well as the length of non-complementary zone between the target regions on the target nucleic acid strands, should not be so long that cooperative binding of probe regions to their respective target regions would be prevented. Moreover, the lengths of the probe and target regions, and complementary target zones, should not be so long that either probe region is able to hybridize independently to its target region by virtue of increased length (and therefore increased annealing temperature) without requiring prior transient hybridization of the other probe region to its target region, and stable hybridization between the complementary target zones. Only when both complementary target zones stably hybridize to one another, and both probe regions stably hybridize to their respective target regions will a signal above a threshold be indicative of the presence of the target nucleic acid be produced.

According to practice of the invention, the target nucleic acids and the nucleic acid probes of the invention can be DNA, RNA or synthetic DNA molecules having modified backbones such as with sulfate or peptide bonds rather than phosphate bonds.

While it is recognized that detectable signals can be produced in the absence of stable hybridization, those of skill in the art recognize that the presence or absence of stable hybridization can be determined by a comparison of signals produced by both negative and positive controls and that signal thresholds can be determined that allow making distinctions between stable and unstable (including transient) hybridization indicative of the presence or absence of a target nucleic acid sequence in a sample. According to one method, the threshold for designating a "positive" reaction can be selected as the mid-point between the lowest value for positive control samples and the highest value for negative control samples under a selected set of conditions.

According to a preferred aspect of the present invention, the first probe region and the second probe region are exactly complementary to the first and second target regions respectively, but they need not be. According to a preferred aspect of the present invention, the first CTZ and the CTZ are exactly complementary to the first and second target regions respectively, but they need not be. According to a preferred aspect of the present invention, the sample/target nucleic acid strand or strands are derived from a human subject, but they need not be.

The present invention has two (or more) sequences on the same probe. The two separate portions of the gap probes in the present invention would be too short to sufficiently bind by themselves. Probe regions may be initially designed based on the unique sequence present on the alleles that one would like to detect. Once that initial design consideration has been addressed, the length of the probe regions generally becomes the next important design factor. Consideration of probe region length is especially critical in those contexts where the undesired sequences differ from the desired target sequence by only a few base pairs (including those cases where there is only a single base pair difference). Binding (stable hybridization) of both probe regions is necessary for a positive signal.

BRIEF DESCRIPTION OF THE DRAWINGS

FIGS. 1A (and 1A') and 1B depict a first embodiment of the present invention wherein the first target region is 3' to the second target region and separated by an intervening sequence on the sample target; and FIGS. 2A (and 2A') and 2B depict a second embodiment of the present invention wherein the first target region is contiguous with the second target region on the sample target and the diagnostic probe comprises a spacer sequence disposed between the first probe region and the second probe region.

FIGS. 3A (and 3A') and 3B depict a third embodiment of the present invention wherein the first target region is 3' to the second target region and separated by an intervening sequence on the sample target, and the diagnostic probe comprises a spacer sequence disposed between the first probe region and the second probe region.

DETAILED DESCRIPTION

Figure 4A:
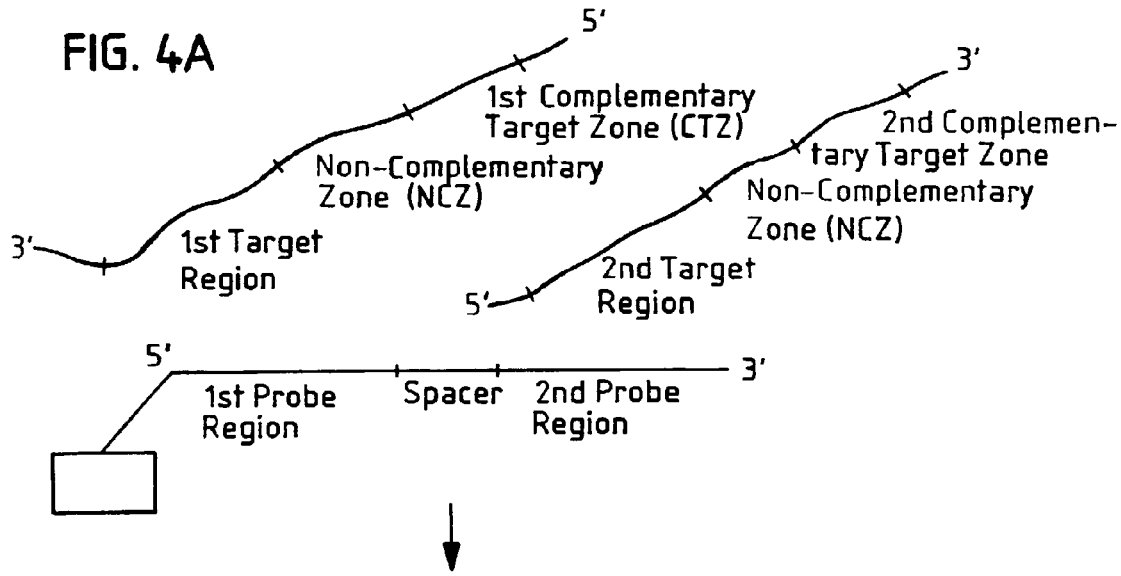
FIGS. 4A, 4B, 4C and 4D depict a fourth embodiment of the present invention wherein the first target region is 3' to the first complementary target zone on the first target nucleic acid strand, and the second target region is 5' to the second complementary target zone.

The present invention relates to nucleic acid probes that may be used in a variety of manners but which are particularly useful for detecting the presence of particular target nucleotide sequences. Rather than using a conventional probe, the present invention provides a diagnostic probe that comprises two (or more) nucleic acid probe regions on the same probe sequence that are preferably non-contiguous. According to the invention, the two portions of the probe sequence, the first and second probe regions, function to specifically bind to the first and second target regions, respectively. The second probe region is coupled at the 3'-end of the first probe region. The second probe region is preferably separated downstream from the first probe region, but may be contiguous if the target regions on the sample nucleic acid strand are not contiguous.

According to practice of the invention, one of the probe regions functions to initially, transiently bind the probe to the sequence of interest on the sample nucleic acid strand. Both of the probe regions can play this role, which means either probe region can transiently bind first. With one of the probe regions transiently bound, the other probe region is thereby more favorably disposed kinetically (by virtue of a local concentration effect) such that it can thereafter more readily recognize another nearby sequence (usually within a few hundred base pairs). Both probe regions can function to increase the specificity of the diagnostic probe for a particular allele or other target sequence.

The length of each probe region should be selected to be below the length that would otherwise stably hybridize by itself to the target sequence under the selected hybridization conditions, in order to prevent a false positive signal. Transient annealing of one of the probe regions to its target region will increase the local concentration of the other probe region to its target region, thus achieving successful annealing of the other region to its target region and the stable hybridization of the probe to the sample.

According to one aspect of this invention, the first and second probe regions are designed such that under given selected hybridization conditions, formation of a detectable reaction product occurs when both probe regions are substantially complementary to their respective target regions, and no reaction product that is detectable above a threshold indicative of the presence of the target sequence occurs under those same hybridization conditions when either probe region is not substantially complementary to its respective target region. It will be understood that the selectivity of the diagnostic probes of the invention is dependent upon the hybridization conditions selected for practice. Thus, those of skill in the art will recognize that higher annealing temperatures will generally require longer probe region sequences while lower annealing temperatures will generally require shorter probe region sequences. Other factors such as reagent concentrations and the GC content of the probe and the sample nucleic acid strand will also affect the design of the diagnostic probes and selection of hybridization conditions for practice of the invention.

FIG. 1 depicts an embodiment of the present invention whereby a diagnostic probe comprising the first and second probe regions that are not separated by a spacer region serves to detect the presence of a target nucleic acid sequence on a sample nucleic acid strand. Specifically, FIG. 1A depicts the transient hybridization of the first probe region to the first target region that is 3' to and separated by an intervening sequence from the second target region on the sample nucleic acid. FIG. 1A' depicts the transient hybridization of the second probe region to the second target region that is 5' to and separated by an intervening sequence from the first target region on the sample nucleic acid.

Transient hybridization of one probe region to its corresponding target region creates a local concentration effect such that, under the selected hybridization conditions, the other probe region of the diagnostic probe will stably hybridize to its target region on the sample nucleic acid sequence. The hybridization conditions are further selected given the identity of the target and the diagnostic probe so that the diagnostic probe is not stably hybridized to the target nucleic acid strand to form a detectable probe:target hybrid when either the first probe region is not substantially complementary to the first target region or the second probe region is not substantially complementary to the second target region. FIG. 1B depicts hybridization of both probe regions of the diagnostic probe to their respective target regions on the sample nucleic acid respectively and the formation of a loop by the intervening sequence between the target regions on the sample nucleic strand, which have hybridized to portions of the diagnostic probe. In FIG. 1B, a stable probe:target hybrid has formed.

FIG. 2 depicts a second embodiment of the present invention whereby a diagnostic probe comprising the first and second probe regions separated by a spacer region is used to detect the presence of a target nucleic acid strand. In this case, the first target region is associated with a second target region that is contiguous with the first target region on the target nucleic acid strand. Specifically, FIG. 2A depicts the transient hybridization of the first probe region to the first target region, which is 3' to the second target region on the target nucleic acid. FIG. 2A' depicts the transient hybridization of the second probe region to the second target region, which is 5' to the first target region on the target nucleic acid.

FIG. 2B depicts hybridization of the first and second probe regions of the diagnostic probe to the first and second target regions on the sample nucleic acid strand respectively and the formation of a loop by the spacer region between the probe regions that is not complementary to the sequence of the sample/target nucleic acid strand. In FIG. 2B, a stable probe:target hybrid has formed.

FIG. 3 depicts a third embodiment of the present invention whereby a diagnostic probe comprising the first and second probe regions separated by a spacer region is used to detect the presence of a target nucleic acid strand. In this embodiment, the first target region is associated with a second target region that is separated by an intervening sequence from the first target region on the target nucleic acid strand. Accordingly, FIG. 3 depicts an embodiment that combines features of the embodiments shown in FIG. 1 and FIG. 2. Specifically, FIG. 3A depicts the transient hybridization of the first probe region to the first target region, which is 3' to the second target region on the target nucleic acid. FIG. 3A' depicts the transient hybridization of the second probe region to the second target region, which is 5' to the first target region on the target nucleic acid.

FIG. 3B depicts hybridization of the first and second probe regions of the diagnostic probe to the first and second target regions on the sample nucleic acid strand respectively and the formation of a loop by the spacer region between the probe regions, and the formation of a loop by the intervening sequence between the target regions such that the two loops are not substantially complementary to one another. In FIG. 3B, a stable probe:target hybrid has formed.

While the first target region is shown 3' to the second target region in the target nucleotide strand in FIGS. 1, 2 and 3, that is for illustrative purposes only. In other embodiments, the first target region may be 5' to the second target region. Embodiments with more than two target regions and more than two probe regions are also contemplated.

In still other embodiments of this invention, the probe regions can hybridize to target regions, wherein the target regions are located on different target nucleic acid strands, and additionally there is at least one zone on one of the target nucleic acid strands that is substantially complementary to a zone on the other target nucleic acid strand.

There is then a first target nucleic acid strand that contains at least two sequences of interest. The first sequence of the first target nucleic acid strand is a first target region, that is substantially complementary to the first probe region. The second sequence of the first target nucleic acid strand is a first complementary target zone (CTZ), which is substantially complementary to a second complementary target zone (CTZ) in the second target nucleic acid strand. The first CTZ may be separated from the first target region by a first non-complementary zone (NCZ), which is preferably less than 350 nucleotide bases in length (0-350 bases), but can be as many as 500 nucleotide bases or more in length.

There is then a second target nucleic acid strand that contains at least two sequences of interest. The first sequence of the second target nucleic acid strand is a second target region that is substantially complementary to the second probe region. The second sequence of the second target nucleic acid strand is a second complementary target zone (CTZ), which is substantially complementary to the first complementary target zone (CTZ) in the first target nucleic acid strand. The second CTZ may be separated from the second target region by a second non-complementary zone (NCZ), which is preferably less than 350 nucleotide bases in length (0-350 bases), but can be as many as 500 nucleotide bases or more in length.

The same principles discussed in the earlier embodiments and aspects of the invention also apply to this and other embodiments involving CTZs, at least in so far as hybridization properties are concerned. Specifically, substantial complementarity between both the first probe region and the first target region, and between the second probe region and the second target region is necessary for stable hybridization. Moreover, in such embodiments involving CTZs, in order for there to be stable hybridization between the first probe region and first target region, and between the second probe region and the second target region, the first CTZ must be substantially complementary to the second CTZ. However, unlike the earlier embodiments, those embodiments involving CTZs, do not necessitate the first probe region to be 5' to the second probe region.

Figure 4B:
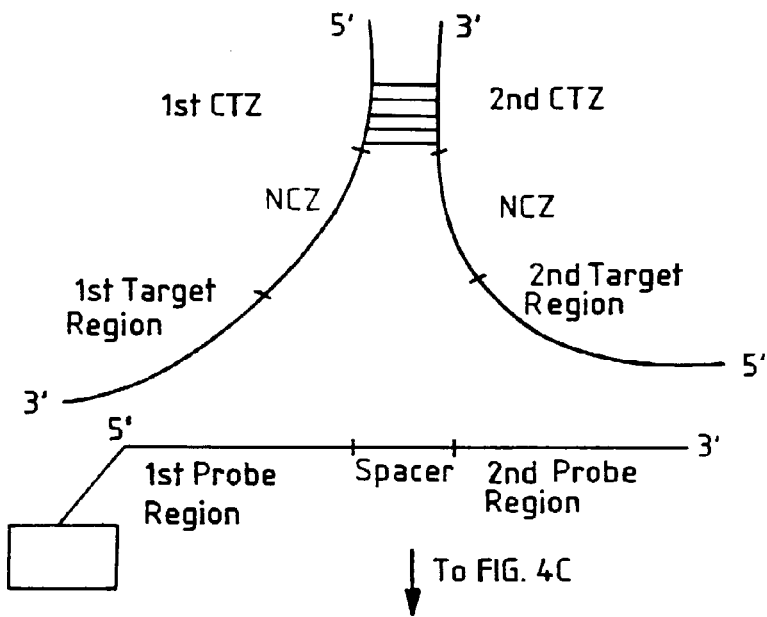
Figure 4C:
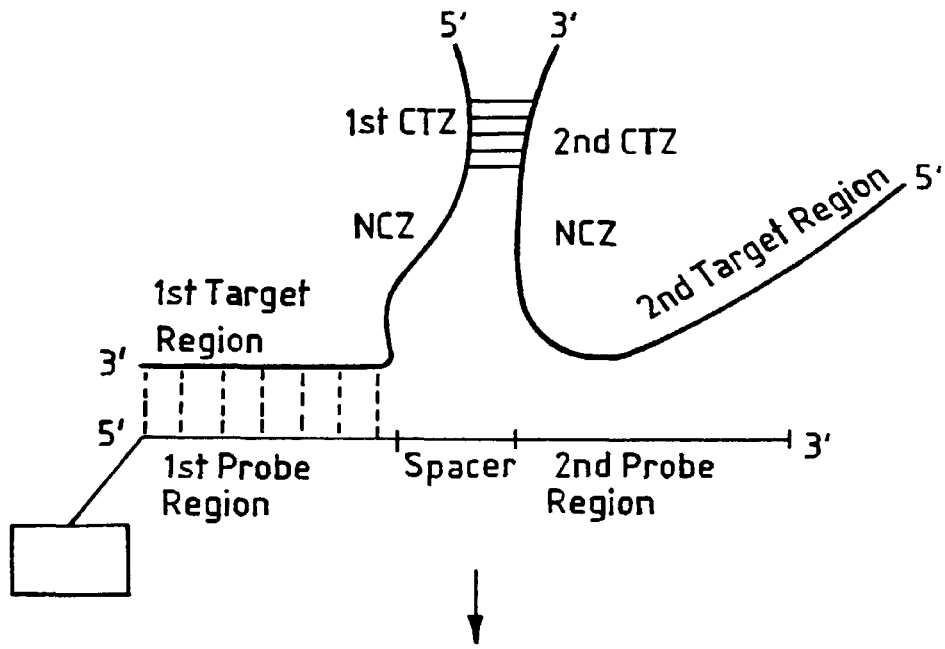
Figure 4D:
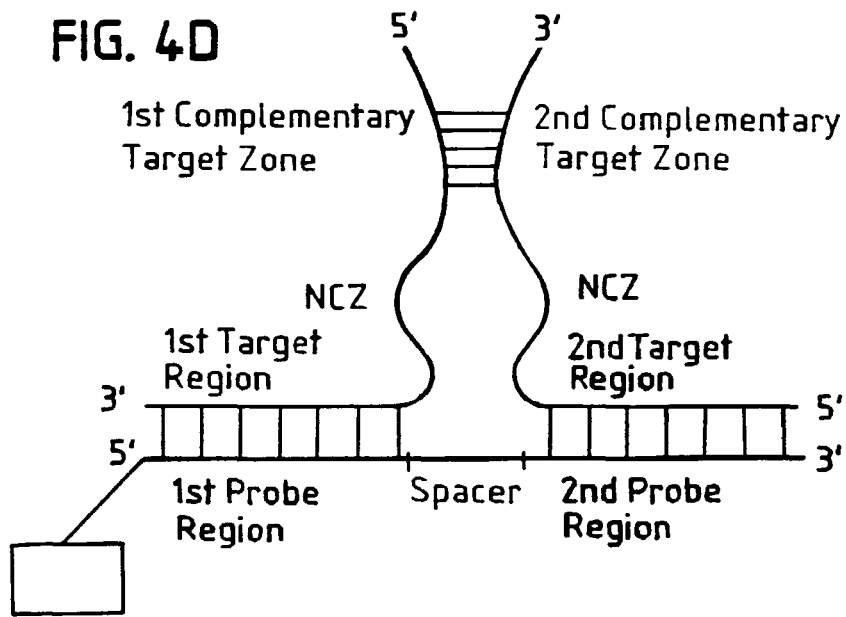

FIG. 4 depicts a fourth embodiment of the present invention whereby a diagnostic probe, comprising first and second probe regions separated by a spacer region with the first probe region 5' to the second probe region, is used to detect the presence of two target nucleic acid strands. In this embodiment, a first target region and first CTZ is on a first target nucleic acid strand, and a second target region and second CTZ is on a second target nucleic acid strand. Specifically, FIG. 4A depicts the first and second target nucleotide strands and the diagnostic probe before any hybridization has occurred. FIG. 4B depicts the stable hybridization between the first and second CTZs. FIG. 4C depicts the transient hybridization of the first probe region to the first target region, the latter of which is 3' to the first CTZ on the first target nucleic acid. In FIG. 4D, a stable probe: target hybrid has formed.

While FIG. 4 shows the first CTZ 5' to the first target region, and the second CTZ 3' to the second target region, in other embodiments the CTZs need not be so positioned. That is, the CTZs may be located differently relative to the target region(s) on the same nucleic acid strand. For example, the first CTZ could be located 3' relative to the first probe region, rather than 5'. Another embodiment could comprise the second CTZ located 5' relative to the second target region, rather than 3'. Yet another embodiment could comprise both the first CTZ 3' relative to the first probe region, and the second CTZ located 5' relative to the second target region. Moreover, while FIG. 4 shows the first probe region located 5' relative to the second probe region, that need not be the case. For example, in other embodiments, the first probe region could be located 3' to the second probe region. Furthermore, embodiments involving CTZs, may or may not comprise a spacer as part of the diagnostic probe, and may or may not include a NCZ in either or both of the target nucleic acid strands.

In embodiments involving CTZs, it is understood that there may be more than one pair of CTZs, that is, there may be multiple zones of complementarity between the two (or more) target nucleic acid strands. One or more CTZs in a given embodiment may be incorporated into a target nucleic strand via a polymerase chain reaction (PCR). Specifically, when a PCR reaction is used to generate a target nucleic acid strand, one or more of the primers used in the PCR reaction may incorporate a zone of nucleic acids that is complementary to a zone of nucleic acids in another target nucleic acid strand. In those embodiments with multiple CTZ pairs, a NCZ may separate two CTZ in a given nucleotide strand.

In the FIGS. 1-4, the diagnostic probe is shown attached to a solid support at the 5'-end of the probe. However, that depiction is for illustrative purposes only. Diagnostic probes according to this invention may also be attached at the 3'-end of the probe, or at other positions as well.

Target nucleic acid strands according to this invention may be derived from any source natural or artificial, including human subjects.

Use of the diagnostic probes according to the methods of the invention will add selectivity to the hybridization assays, because more than two unique sequences can be used as the selection criteria for the detection. Thus, the number of separate detections steps required for assigning an unknown allele may be reduced, which reduces the overall cost of allele analysis. Selection of an appropriate diagnostic probe according to the invention will allow resolution of ambiguities that occur in some heterozygous cases wherein the detection pattern derived from two different alleles is identical to another pair of alleles using probes with conventional designs.

The use of diagnostic probes according to the methods of the invention allows greater specificity in the recognition of a specific allele or set of alleles by using more than one region of sequence homology to the nucleic acid sequence of interest. Increasing the specific recognition of nucleic acid sequence homology refines the ability to carry out a variety of DNA-based tests. Included among these tests would be HLA tissue typing, detection of genetically inherited diseases, detection of infectious organisms in tissue, or detection of a variety of other markers or conditions based on the presence of a nucleic acid sequence (e.g. for testing the efficacy of a gene therapy technique).

The term "nucleotide" as used herein can refer to nucleotides present in either DNA or RNA and thus includes nucleotides that incorporate adenine, cytosine, guanine, thymine and uracil as base, the sugar moiety being deoxyribose or ribose. It will be appreciated, however, that other modified bases capable of base pairing with one of the conventional bases, adenine, cytosine, guanine, thymine and uracil, may be used in the diagnostic probe employed in the present invention. Such modified bases include, for example, 8-azaguanine and hypoxanthine.

The term "complementary to" is used herein in relation to nucleotides to mean a nucleotide which will base pair with another specific nucleotide. Thus, adenosine triphosphate is complementary to uridine triphosphate or thymidine triphosphate and guanosine triphosphate is complementary to cytidine triphosphate. It is appreciated that while thymidine triphosphate and guanosine triphosphate may base pair under certain circumstances, they are not regarded as complementary for the purpose of this specification. It will also be appreciated that while cytosine triphosphates and adenosine triphosphate may base pair under certain circumstances, they are not regarded as complementary for the purposes of this specification. The same applies to cytosine triphosphate and uracil triphosphate.

The term "cis" is used to refer to the situation where two (or more) target regions are located on the same DNA strand, i.e. they are part of the same allele. In contrast, the term "trans" is used to refer to the situation where two (or more) target regions are on two different DNA strands, i.e. they are part of different alleles.

The term "contiguous" refers to the case where two sequences, regions, zones, stretches, etc. of nucleic acids are immediately adjacent to one another and located on the same strand of nucleic acid. That is, there is no spacer, intervening sequence or non-complementary zone between the two sequences.

The diagnostic probe regions herein are selected to be "substantially" complementary to the different strands of each specific sequence to be detected. This means that the diagnostic probes must be sufficiently complementary to hybridize with their respective strands. Therefore, the diagnostic probe sequence need not reflect the exact sequence of the sample/target nucleic acid sequence. Thus, probe sequences (including the first and second probe regions in the diagnostic probe) do not necessarily have to be exactly complementary to the target sequences. Thus, not all probes produce a clean negative signal similar to that of a negative control for negative alleles. Depending upon the number of mismatches and what types of mismatches (G-T mismatch occasionally produces approximately the same signal as G-C match), the fluorescent signal for 1 base-pair mismatched alleles might produce a signal substantially higher than the negative control. However, as long as the signal of the true positive alleles are significantly higher than those potentially cross-reacting alleles, usually > by 10-20%, a threshold or cut-off value can be established to distinguish between positive and negative reactions.

Generally a small number of mismatches will be tolerated in the middle of the probe sequences and will allow for hybridization. In general, the degree of mismatching tolerated depends upon the probe region length, which in turn affects the denaturation temperature and the annealing temperature selected. If the denaturation temperature of the probe is close to or higher than the annealing temperature (less stringent), then the probe will still adhere to the target sequence despite a small number of (generally one or two or at most three) mismatches. A probe region may be capable of tolerating more mismatches in the middle of the sequence but its ability to do so depends on the denaturation temperature of the probe region and the annealing temperature of the selected hybridization and detection conditions. Similar parameters apply to complementary target zone sequences. It is preferred that the first and second probe regions, as well as the first and second complementary zones be exactly complementary to their respective target regions or zones. However, these regions and zones need not be exactly complementary.

A diagnostic sequence-specific oligonucleotide-probe detection (SSO) system is a system or device that uses a diagnostic probe to assay for the presence of a particular target nucleic acid sequence. In such a system or device, the diagnostic probes may be attached to a support using linkers such as are well known in the art including the use of poly-carbon and poly-nucleotide linkers. Alternatively, target sequences can be immobilized on a solid support, such as a nitrocellulose membrane and the diagnostic probe is in solution. The diagnostic probe in the SSO includes at least one probe region. The term "probe region" refers to a nucleotide sequence on a diagnostic probe substantially complementary to a portion of the target nucleotide sequence. This substantially complementary portion of the target nucleotide strand is referred to as a "target region." Those embodiments involving multiple target nucleotide strands may have a "complementary target zone" (CTZ), a particular nucleotide sequence, in each target nucleotide strand such that the CTZ in one target strand is substantially complementary to a CTZ in another target strand. The sequence separating a target region from a CTZ in a particular target nucleotide strand is termed a non-complementary zone (NCZ), such that the NCZ in one target strand is not substantially complementary to a NCZ in another target strand. However, a NCZ need not be present.

A gap probe refers to a particular kind of a diagnostic probe that contains more than one probe region. The gap probe may or may not have a spacer between its probe regions. A "spacer" refers to a nucleotide sequence between two probe regions, which is not substantially complementary to the intervening sequence, if present, between the corresponding target regions of the target nucleotide sequence. A "spacer" is also not substantially complementary to a non-complementary zone, if present, between a target region and CTZ of a target nucleotide sequence. A probe:target hybrid is a complex comprising the diagnostic probe stably annealed to the target nucleotide sequence.

Labeling can be either on the probes or on the target sequences. Direct fluorescence compounds, biotin, FITC or Digoxigenin(Dig) can be used as the tag. For the indirect detection, fluorescence or enzyme conjugated Avidine/Strepavidine (for biotin), anti-FITC antibody (for FITC), anti-Dig antibody (for Dig) will be used for detection purposes. According to one embodiment, latex beads modified with a carboxyl group can be used to immobilize probes. The carboxyl group on the beads is first activated by 1-ethyl-3-(3-dimethylaminopropyl) carbodiimide hydrochloride (EDC) and then the EDC-activated carboxyl group is reacted with the amine group at the 5' end of the oligo probes. Alternative embodiments using chemistries to link amine to amine, sulfide to amine and other chemistries may also be practiced.

Other aspects and advantages of the present invention will be understood upon consideration of the following illustrative examples.

Example 1

According to this example, a single diagnostic gap probe according to this invention comprising a first probe region and a second probe region, was used to distinguish the HLA DRB1*0308 and DRB1*1107 alleles from other DRB1 alleles. Thus, the conventional probe, OLR4040 (5'-GCCT-GATGAGGAGTACTG-3') (SEQ ID NO: 5), was designed to detect GAG at amino acid position 58 of DRB1. Probe OLR-4093-2 (5'-AAGCGGGGCCGGGTG-3') (SEQ ID NO: 6) recognizes the complement of AAG CGG GGC (SEQ ID NO: 8) at amino acid position 71-72 of DRB1. However, DRB1*0308 and DRB1*1107 contain both sequences and hybridize to both probes. Thus, these alleles contribute to many ambiguities when analyzing DRB1 heterozygous reaction patterns. Table 1, below sets out the relationship between the sequences of these DRB1 alleles and the gap and conventional probes used to detect them.

Table 1 displays the characteristic sequences of allelic regions and probe sequences. Alleles in this example comprise two sequence regions termed "Region 1" and "Region 2", respectively. The amino acid positions for each region are also provided. Sequences in the table read from left to right, and a sequence ends when the end of a row or when double slashes "//" are reached, whichever occurs first. The result is a contiguous sequence. For example, the Reference (Allele) comprises both SEQ ID NOS: 1 and 2. SEQ ID NO: 1 is a contiguous sequence, corresponding to Region 1, and begins "CGG" and ends "TGG" at the "//". SEQ ID NO: 2 is a contiguous sequence, corresponding to Region 2, and begins "GAG" and ends "GTG."

For sequence types other than the Reference, where a "-" appears, a particular sequence comprises the nucleotide base at the corresponding position of the Reference (Allele). When a nucleotide "letter" appears instead of a "-", a particular sequence comprises that nucleotide instead of the reference nucleotide at the corresponding position. In the absence of "-" or nucleotide "letter", the particular sequence does not include a nucleotide base corresponding to that position. The table is then read straight across until a "//" is reached or the end of the row is reached, whichever comes first, to form a contiguous sequence. (In some tables, a row may continue onto a subsequent page.) In the case of probes, the reader will appreciate that there is no "//", so the sequence reads straight across to form a single contiguous sequence, instead of two separate continguous sequences as is the case with alleles.

Probe OLR-4431-3 includes an intermediary region (inter-region). An intermediary region does not correspond to allelic sequence, but instead artificial sequence. Examples of artificial sequence include the "spacer" in a diagnostic probe, e.g. the "TTTT" of Probe OLR-4431-3. The reader will also appreciate that more than one allele may share a particular sequence identification (ID) number, because the alleles share a common sequence for that particular region. For example, the Reference Allele DRB1*0101 and the DRB1*03011 series of Alleles in Table 1 both share a common sequence for Region 1, which corresponds to SEQ ID NO: 1. However, these two allelic series differ in respect to Region 2.

An organizational scheme similar to that just described for Table 1 is also employed in Tables 3, 5, 7, 9 and 11.

TABLE 1

Sequence Alignment of DRB1 Allele Target Sequences and Probes

| Sequence Type | Sequence Name(s) and Corresponding Relevant Sequence ID Numbers | Region 1 (Numbers in First Row Below Refer to Relevant Amino Acid Positions of Nucleotides in Subsequent Rows) | | | | | | | Inter-Region |
|---|---|---|---|---|---|---|---|---|---|
| | | 55 | 56 | 57 | 58 | 59 | 60 | 61 | |
| Reference Allele | DRB1*0101 (SEQ ID NOS: 1 and 2) | CGG | CCT | GAT | GCC | GAG | TAC | TGG | // |
| Alleles | DRB1*0415, DRB1*11011/012/041/042/05/06/081/082/09/10/121/122/13/15/18/19/22/24/26-30/34/37/39 (SEQ ID NOS: 3 and 2) | — | — | — | —AG | — | — | — | // |
| Alleles | DRB1*0308, DRB1*1107 (SEQ ID NOS: 3 and 4) | — | — | — | —AG | — | — | — | // |
| Alleles | DRB1*03011/012/021/022/03-07/09/14-16/18, DRB1*0422, DRB3*0204 (SEQ ID NOS: 1 and 4) | — | — | — | — | — | — | — | // |
| Probe | OLR-4040 (SEQ ID NO: 5) | — | — | — | —AG | — | — | — | |
| Reference Allele | DRB1*0101 (SEQ ID NOS: 1 and 2) | CGG | CCT | GAT | GCC | GAG | TAC | TGG | // |
| Probe | OLR-4043-2 (SEQ ID NO: 6) | | | | | | | | |
| Probe | OLR-4431-3 (SEQ ID NO: 7) | | — | — | —AG | — | — | | TTTT |

| Sequence Type | Sequence Name(s) and Corresponding Relevant Sequence ID Numbers | Region 2 (Numbers in First Row Below Refer to Relevant Amino Acid Positions of Nucleotides in Subsequent Rows) | | | | | | |
|---|---|---|---|---|---|---|---|---|
| | | 69 | 70 | 71 | 72 | 73 | 74 | 75 |
| Reference Allele | DRB1*0101 (SEQ ID NOS: 1 and 2) | GAG | CAG | AGG | CGG | GCC | GCG | GTG |
| Alleles | DRB1*0415, DRB1*11011/012/041/042/05/06/081/082/09/10/121/122/13/15/18/19/22/24/26-30/34/37/39 (SEQ ID NOS: 3 and 2) | — | — | — | — | — | — | — |

TABLE 1-continued

Sequence Alignment of DRB1 Allele Target Sequences and Probes

| | | | | | | | | |
|---|---|---|---|---|---|---|---|---|
| Alleles | DRB1*0308, DRB1*1107 (SEQ ID NOS: 3 and 4) | — | — | —A— | — | —G— | CG— | — |
| Alleles | DRB1*03011/012/021/022/03-07/09/14-16/18, DRB1*0422, DRB3*0204 (SEQ ID NOS: 1 and 4) | — | — | —A— | — | —G— | CG— | — |
| Probe | OLR-4040 (SEQ ID NO: 5) | | | | | | | |
| Reference Allele | DRB1*0101 (SEQ ID NOS: 1 and 2) | GAG | CAG | AGG | CGG | GCC | GCG | GTG |
| Probe | OLR-4043-2 (SEQ ID NO: 6) | | | —A— | — | —G— | CG— | — |
| Probe | OLR-4431-3 (SEQ ID NO: 7) | — | — | —A— | — | —G | | |

The conventional approach to resolving the ambiguities caused by the DRB1*0308 and DRB1*1107 alleles is to perform a second round of PCR that will only amplify either the DRB1*03xx or the DRB1*11xx and then repeat the probe hybridization. Accordingly, it is very advantageous to detect the presence of DRB1*0308 and DRB1*1107 so as to distinguish those alleles from other similar alleles during the first round of PCR and probe hybridization in order to avoid a further round of PCR and hybridization.

Specifically, a DNA hybridization reaction between amplified HLA gene and probes immobilized on microspheres was carried out as follows. Standard gene amplification reactions containing approximately 1 ng/microliter of genomic DNA and 10 micromolar of corresponding sequence-specific biotinylated primers were set up using a pre-optimized thermocycling program. 5 microliters of resulting mixture containing amplified HLA-DRB1 exon 2 region was denatured, neutralized and were mixed with desired probe-bound microspheres (1000 microspheres per probe per test) in 1M NaCl and 70 mM sodium phosphate buffer. The hybridization reactions were incubated at 60° C. for 15 minutes. Then the 2 volumes of 50 nM NaCl solution (pre-heated at 60° C.) was added to the mixtures, and the tubes were centrifuged for 5 minutes. Supernatant was removed without disturbing the pelleted microspheres. This washing step was repeated two more times.

The hybridized DNA was then labeled by addition of 3 volumes of 5 micrograms per milliliter of phycoerythrin-streptavidin conjugate. The labeling mixture was incubated at 60° C. for five minutes and washed as described above. Washed microspheres were resuspended to 80 microliter volume with 50 nM NaCl. The hybridization signal was detected using a LUMINEX100™ Flow Analyzer that excites, detects and records fluorescence signal at 580 nm for individual microspheres injected into the instrument. Approximately 100 to 200 microspheres per test were analyzed to calculate median fluorescence intensity (MFI) for each probe. Resulting MFI for each probe used in a test are then used to calculate relative hybridization signals using the MFI from appropriate positive control probes.

Positive control probes are probes that recognize a non-polymorphic region on all alleles that can be amplified by a specific primer set. The target nucleic acid strands for this invention include allelic regions that have been amplified using the polymerase chain reaction (PCR). The positive control probes are used to provide reference signal so that variation in the amount of the amplified DNA (amplicons) can be estimated. The positive control signal is used to calculate relative signal of all diagnostic probes as diagnostic probe signals are expressed as percent of positive control signal. The positive control probe sequences for DRB1 Exon 2 is 5'-ggAACAgCCAgAAggAC-3' (SEQ ID NO: 9).

According to the invention, a gap probe designated OLR4431-3 having the sequence: (5'-CTGATGAGGAG-TACTTTTAGCAGAAGCGGGG-3' (SEQ ID NO: 7) has two probe regions designed to hybridize to a target nucleic acid sequence (including DRB1*0308 and DRB1*1107). A first probe region CTGATGAGGAGTAC (SEQ ID NO: 10) can hybridize to a first target region, and a second probe region AGCAGAAGCGGGG (SEQ ID NO: 11) can hybridize to a second target region. The two probe regions are separated by a spacer comprising 4 Ts, which is not designed to hybridize to the target sequence. The gap probe produced fluorescent signals of <1% to DRB1 alleles that contain only GAG at position 58 without AAG CGG GGC (SEQ ID NO: 8) at position 71-73 thus effectively eliminating false positive signals by DRB1 alleles that contain only GAG at position 58 without AAG CGG GGC (SEQ ID NO: 8) at position 71-73. This probe also produced <20% of fluorescent signal to DRB1 alleles containing AAG CGG GGC (SEQ ID NO: 8) at position 71-73 without GAG at position 58. In the data shown in Table 2, below the use of the gap probe with a sample containing DRB1* 0308 generated a signal of almost 90% of the positive control probe signal. Accordingly, a cut-off value, for determining a positive reaction (usually the mid-point between the lowest positive value and the highest negative value), can be readily established. Considering the number of samples that need to be tested in the bone marrow donor registry a significant saving of time and expense is provided by the ability to detect the presence of DRB1*0308 and DRB1*1107 as provided above.

TABLE 2

Fluorescent Signal Intensity of the Probes Compared to the Control Probe

| | | % (Test probe signal/Control probe signal) | | |
|---|---|---|---|---|
| Cell ID | DRB1 Alleles | OLR-4040 (Conventional) | OLR-4093-2 (Conventional) | OLR-4431-3 (Gap Probe) |
| GN0090 | 0308, 0405 | 37.4 | 16.2 | 88.3 |
| TER227 | 03021, 03021 | 0.0 | 31.7 | 16.4 |

TABLE 2-continued

Fluorescent Signal Intensity of the
Probes Compared to the Control Probe

| | | % (Test probe signal/Control probe signal) | | |
|---|---|---|---|---|
| Cell ID | DRB1 Alleles | OLR-4040 (Conventional) | OLR-4093-2 (Conventional) | OLR-4431-3 (Gap Probe) |
| TER118 | 0301, 1202 | 0.0 | 22.9 | 14.3 |
| TER087 | 0301, 0803 | 0.0 | 20.4 | 11.9 |
| TER156 | 1104, 1404 | 35.1 | 0.1 | 0.7 |
| TER119 | 1101, 0101 | 26.3 | 0.0 | 0.5 |
| TER083 | 1102, 0404 | 26.1 | 0.0 | 0.4 |

Example 2

Two of the most common occurring ambiguities in serological level DNA typing at the HLA-A locus using SSO methodology are as follows. First, the high frequency A*03011 and A*2501 heterozygote has the same SSO reaction pattern as the A*3204 and A*6601 heterozygote. Second, the high frequency A*3201 and A*6601 heterozygote has the same SSO reaction pattern as A*2502 and A*7401. The ability to generate a unique probe that recognizes two target regions that are only presented in A*2501 and A*2502 will significantly reduce the need for second-round testing of the above heterozygotes.

In this example, a single diagnostic gap probe, A166-2, composed of two separate probe regions, separated by a short spacer, can distinguish some genotypes of the A*2501-2504 group, from a number of other HLA-A genotypes. Table 3, below sets out the relationship between the sequences of these HLA-A alleles and the gap and conventional probes used to detect them. The use of two conventional probes can determine the presence of two target regions in the genome, but cannot determine whether those target regions are in the same, "cis", or different, "trans", alleles of an allelic pair. Probe A104-11, which has a single recognition sequence, determines the presence of the indicated target nucleic acid sequence from about codon 62 to about codon 68 (table 3). Probe A150-19 also has a single probe region for determining the presence of the indicated target nucleic acid sequence from about codon 77 to about codon 85 (table 3).

TABLE 3

Sequence Alignment of HLA-A Allele Target Sequences and Probes

| Sequence Type | Sequence Name(s) and Corresponding Relevant Sequence ID Numbers | Region 1 (Numbers in First Row Below Refer to Relevant Amino Acid Positions of Nucleotides in Subsequent Rows) | | | | | | | | | Inter-Region |
|---|---|---|---|---|---|---|---|---|---|---|---|
| | | 61 | 62 | 63 | 64 | 65 | 66 | 67 | 68 | 69 | |
| Reference Allele | A*0101 (SEQ ID NOS: 12 and 13) | GAC | CAG | GAG | ACA | CGG | AAT | ATG | AAG | GCC | // |
| Alleles | A*2424, A*2501~04 (SEQ ID NOS: 14 and 16) | —— | —G— | A—C | —— | —— | —— | —G— | —— | —— | // |
| Alleles | A*6601 (SEQ ID NOS: 14 and 13) | —— | —G— | A—C | —— | —— | —— | —G— | —— | —— | // |
| Alleles | A*3201 (SEQ ID NOS: 15 and 16) | —— | —— | —— | —— | —— | —— | —G— | —— | —— | // |
| Alleles | A*0301 (SEQ ID NOS: 15 and 13) | —— | —— | —— | —— | —— | —— | —G— | —— | —— | // |
| Alleles | A*68012 (SEQ ID NOS: 14 and 13) | —— | —G— | A—C | —— | —— | —— | —G— | —— | —— | // |
| Probe | A166-2 (SEQ ID NO: 17) | | —G— | A—C | —— | —— | — | | | | TTTT |
| Probe | A104-11 (SEQ ID NO: 18) | | G— | A—C | —— | —— | —— | —G— | | | |
| Probe | A150-19 (SEQ ID NO: 19) | | | | | | | | | | |

| Sequence Type | Sequence Name(s) and Corresponding Relevant Sequence ID Numbers | Region 2 (Numbers in First Row Below Refer to Relevant Amino Acid Positions of Nucleotides in Subsequent Rows) | | | | | | | | |
|---|---|---|---|---|---|---|---|---|---|---|
| | | 77 | 78 | 79 | 80 | 81 | 82 | 83 | 84 | 85 |
| Reference Allele | A*0101 (SEQ ID NOS: 12 and 13) | C | CTG | GGG | ACC | CTG | CGC | GGC | TAC | TAC |
| Alleles | A*2424, A*2501~04 (SEQ ID NOS: 14 and 16) | — | —— | C— | —T— | GC— | —T— | C— | —— | —— |
| Alleles | A*6601 (SEQ ID NOS: 14 and 13) | — | —— | —— | —— | —— | —— | —— | —— | —— |
| Alleles | A*3201 (SEQ ID NOS: 15 and 16) | — | —— | C— | —T— | GC— | —T— | C— | —— | —— |
| Alleles | A*0301 (SEQ ID NOS: 15 and 13) | — | —— | —— | —— | —— | —— | —— | —— | —— |
| Alleles | A*68012 (SEQ ID NOS: 14 and 13) | — | —— | —— | —— | —— | —— | —— | —— | —— |
| Probe | A166-2 (SEQ ID NO: 17) | | | —— | —T— | GC— | —T— | C— | | |
| Probe | A104-11 (SEQ ID NO: 18) | | | | | | | | | |
| Probe | A150-19 (SEQ ID NO: 19) | — | —— | C— | —T— | GC— | —T— | C— | —— | —— |

TABLE 4

Fluorescent Signal Intensity of the HLA-A
Probes Compared to the Control Probe

| | | % (Test probe signal/Control probe signal) | | |
|---|---|---|---|---|
| Cell ID | HLA-A Alleles | A166-2 | A104-11 | A150-19 |
| 9008 | 2501 | 61.9% | 87.3% | 38.9% |
| TER250 | 2501, 68012 | 46.8% | 90.5% | 29.2% |
| 9057 | 6601 | 0.0% | 72.5% | 0.0% |
| 9035 | 3201 | 0.0% | 0.001% | 56.7% |
| TER259 | 3201, 6802 | 0.0% | 91.4% | 32.8% |

The binding of the gap probe to both target regions indicates the presence of one of the alleles in which both target regions are present and in the cis configuration. This result is distinguishable from one in which both target regions are present, but in the trans configuration. In the trans configuration, the conventional probes bind their target regions if present, but the gap probe does not, because the affinity for only one of the two target regions is not great enough to facilitate stable binding under these conditions. Thus, for instance, a genotype containing an A*2501/A*03011 allele pair is distinguishable from a genotype containing an A*3204/A*6601 allelic pair. A166-2 binds only to a sample with at least one A*25 allele, whereas A104-11 and A150-19 both bind to DNA with either allelic pair.

Probe A104-11 binds well to any DNA (9008, Ter250, 9057, and Ter259) containing its HLA-A target sequence (alleles A*2501, A*68012, A*6601, and A*6802 in this experiment). A150-19 binds well to any DNA (9008, Ter250, 9035, and Ter259) containing its target sequence (alleles A*2501 and A*3201 in this experiment). Heterozygous DNA containing both target sequences in trans, e.g. Ter259 (A*3201/A*6802) would not be distinguishable from one containing both target sequences in cis, e.g. 9008 (homozygous A*2501) or Ter250 (heterozygous A*2501) using only the two conventional probes, A104-11 and A150-19. However, A166-2 binds well only to A*2501 containing DNA's having the cis configuration 9008 (61.9%) and Ter250 (46.8%). The positive control sequence for A locus Exon 2 is 5'-gCTACTACAACCAgAgCgAg-3' (SEQ ID NO: 20).

Example 3

In this example, a gap probe, B204 is be used to determine if two recognition sites are in the cis configuration. Table 5, below sets out the relationship between the sequences of this and other HLA-B alleles and the gap and conventional probes used to detect them. DNA #1067 contains allele B*1521, which has the target region for probe B106, but not for B153. Conversely DNA's #1064 and Ter244 are homozygous for alleles containing the target region for probe B153. DNA #124 contains target regions in HLA-B for both probes B106 and B153. However, the signal for probe B204 is negative for these DNA's because each target region is in a separate allele, i.e. this is the "trans" configuration. The signal for probe B204 is positive for DNA's Ter250 (allele B*1523) and 9035 (B*3801), which contains target regions in the same allele, i.e. the "cis" configuration.

The sequence at amino acid codons 64-68 recognized by probe B106 will recognize at least 73 alleles of the HLA-B locus. However, if the sequence at amino acid 79-83 of probe B153 is included as part of the gap-probe then only about 5 alleles of the HLA-B will be recognized by the B204 gap-probe, thus increasing the resolution of the SSO system utilizing the gap-probes.

TABLE 5

Sequence Alignment of HLA-B Allele Target Sequences and Probes

| Sequence Type | Sequence Name(s) and Corresponding Relevant Sequence ID Numbers | Region 1 (Numbers in First Row Below Refer to Relevant Amino Acid Positions of Nucleotides in Subsequent Rows) | | | | | | | Inter-Region |
|---|---|---|---|---|---|---|---|---|---|
| | | 64 | 65 | 66 | 67 | 68 | 69 | 70 | |
| Reference Allele | A*0101 (SEQ ID NOS: 21 and 22) | ACA | CGG | AAT | ATG | AAG | GCC | CAC | // |
| Alleles | B*1523, B*3801 (SEQ ID NOS: 23 and 24) | —— | —A— | —TC | TGC | —— | A—— | A—— | // |
| Alleles | B*1401, B*1521, B*3901 (SEQ ID NOS: 23 and 25) | —— | —A— | —TC | TGC | —— | A—— | A—— | // |
| Alleles | B*51011, B*5301 (SEQ ID NOS: 26 and 24) | —— | —A— | —TC | T—C | —— | A—— | A—— | // |
| Alleles | B*5501 (SEQ ID NOS: 27 and 25) | —— | —A— | —TC | TAC | —— | —— | ——G | // |
| Alleles | B*4601 (SEQ ID NOS: 28 and 25) | —— | —A— | ——G | TAC | —— | CG— | ——G | // |
| Probe | B204 (SEQ ID NO: 29) | —— | —A— | —TC | TGC | —— | | | TTT |
| Probe | B153 (SEQ ID NO: 30) | | | | | | | | |
| Probe | B106 (SEQ ID NO: 31) | —— | —A— | —TC | TGC | —— | A—— | | |

| Sequence Type | Sequence Name(s) and Corresponding Relevant Sequence ID Numbers | Region 2 (Numbers in First Row Below Refer to Relevant Amino Acid Positions of Nucleotides in Subsequent Rows) | | | | | | |
|---|---|---|---|---|---|---|---|---|
| | | 77 | 78 | 79 | 80 | 81 | 82 | 83 |
| Reference Allele | A*0101 (SEQ ID NOS: 21 and 22) | AAC | CTG | GGG | ACC | CTG | CGC | GGC |
| Alleles | B*1523, B*3801 (SEQ ID NOS: 23 and 24) | —— | —— | C—— | —T— | GC— | —T— | C—— |
| Alleles | B*1401, B*1521, B*3901 (SEQ ID NOS: 23 and 25) | —G— | —— | C—— | —A— | —— | —— | —— |
| Alleles | B*51011, B*5301 (SEQ ID NOS: 26 and 24) | —— | —— | C—— | —T— | GC— | —T— | C—— |

TABLE 5-continued

Sequence Alignment of HLA-B Allele Target Sequences and Probes

| | | | | | | | | | |
|---|---|---|---|---|---|---|---|---|---|
| Alleles | B*5501 (SEQ ID NOS: 27 and 25) | —G— | | C— | —A— | | | | |
| Alleles | B*4601 (SEQ ID NOS: 28 and 25) | —G— | | C— | —A— | | | | |
| Probe | B204 (SEQ ID NO: 29) | | | | —T— | GC— | —T— | C— | |
| Probe | B153 (SEQ ID NO: 30) | | | C— | —T— | GC— | —T— | C | |
| Probe | B106 (SEQ ID NO: 31) | | | | | | | | |

TABLE 6

Fluorescent Signal Intensity of the HLA-B Probes Compared to the Control Probe

| | | % (Test probe signal/Control probe signal) | | |
|---|---|---|---|---|
| Cell ID | HLA-B Alleles | B204 | B153 | B106 |
| 9035 | 3801/3801 | 108.6% | 117.0% | 122.5% |
| TER250 | 1523/5501 | 85.7% | 90.6% | 191.1% |
| #124 | 1401/51011 | 1.8% | 71.3% | 57.6% |
| #1064 | 5301/5301 | 1.6% | 115.3% | 0.0% |
| TER244 | 51011/51011 | 1.7% | 125.1% | 0.0% |
| #1067 | 1521/4601 | 0.74% | 0.25% | 65.9% |

In Table 6, the high signals for probe B153 indicate that it recognizes HLA-B target sequences in DNAs 9035, Ter250, #124, #1064, and Ter244 corresponding to alleles B*3801, B*1523, B*51011, and B*5301, and B*51011, respectively. Similarly, B106 recognizes sequences in DNA's 9035, Ter250, #124, and #1067 corresponding to alleles B*3801, B*1523, B*1401, and B*1521, respectively. The results using these two conventional probes do not differentiate whether target sequences are in the trans configuration, e.g. in DNA #124 (B*1401/B*51011) or in the cis configuration, e.g. in DNA's 9035 (B*3801) or Ter250 (B*1523). The high signal for probe B204 only with 9035 (B*3801) and Ter250 (B*1523) DNAs demonstrates that the cis configuration for the two separate target sequences is present. The positive control sequence for B locus Exon 2 is 5'-gCTACTACAACCAgAgCgA-3' (SEQ ID NO: 32).

Example 4

This example concerns the DQB1 locus of HLA class II. Probe DQ25-8 recognizes a target region characteristic of DQB1*05031 and of DQB1*06011, whereas DQ33 recognizes a separate target region characteristic of DQB1*05011 and of DQB1*05031. However, the use of probe DQ54G-3, which recognizes both probe regions, but only in the cis configuration, determines whether DQB1*05031 is at least one of the two alleles. Table 7, below sets out the relationship between the sequences of these HLA-DQB1 alleles and the gap and conventional probes used to detect them.

TABLE 7

Sequence Alignment of HLA-DQB1 Allele Target Sequences and Probes

| Sequence Type | Sequence Name(s) and Corresponding Relevant Sequence ID Numbers | Region 1 (Numbers in First Row Below Refer to Relevant Amino Acid Positions of Nucleotides in Subsequent Rows) | | | | | | | | Inter-Region |
|---|---|---|---|---|---|---|---|---|---|---|
| | | 52 | 53 | 54 | 55 | 56 | 57 | 58 | 59 | |
| Reference Allele | DQB1*05011 (SEQ ID NOS: 33 and 34) | CCG | CAG | GGG | CGG | CCT | GTT | GCC | GAG | // |
| Alleles | DQB1*05031 (SEQ ID NOS: 35 and 34) | — | — | — | — | — | —AC | — | — | // |
| Alleles | DQB1*06011 (SEQ ID NOS: 35 and 36) | — | — | — | — | — | —AC | — | — | // |
| Alleles | DQB1*05011 (SEQ ID NOS: 33 and 34) | — | — | — | — | — | — | — | — | // |
| Probe | DQ54G-3 (SEQ ID NO: 37) | | | | | — | —AC | — | | TTTT |
| Probe | DQ25-8 (SEQ ID NO: 38) | — | | | | | —AC | — | | |
| Probe | DQ33 (SEQ ID NO: 39) | | | | | | | | | |

| Sequence Type | Sequence Name(s) and Corresponding Relevant Sequence ID Numbers | Region 2 (Numbers in First Row Below Refer to Relevant Amino Acid Positions of Nucleotides in Subsequent Rows) | | | | | | |
|---|---|---|---|---|---|---|---|---|
| | | 68 | 69 | 70 | 71 | 72 | 73 | 74 |
| Reference Allele | DQB1*05011 (SEQ ID NOS: 33 and 34) | CTG | GAG | GGG | GCC | CGG | GCG | TCG |
| Alleles | DQB1*05031 (SEQ ID NOS: 35 and 34) | — | — | — | — | — | — | — |
| Alleles | DQB1*06011 (SEQ ID NOS: 35 and 36) | — | — | A— | A— | —A | — | GA— |
| Alleles | DQB1*05011 (SEQ ID NOS: 33 and 34) | — | — | — | — | — | — | — |
| Probe | DQ54G-3 (SEQ ID NO: 37) | — | — | — | — | | | |

TABLE 7-continued

Sequence Alignment of HLA-DQB1 Allele Target Sequences and Probes

| | | | | | | | | |
|---|---|---|---|---|---|---|---|---|
| Probe | DQ25-8 (SEQ ID NO: 38) | | | | | | | |
| Probe | DQ33 (SEQ ID NO: 39) | — | — | — | — | — | — | — |

TABLE 8

Fluorescent Signal Intensity of the HLA-DQB1 Probes Compared to the Control Probe

| | | % (Test probe signal/Control probe signal) | | |
|---|---|---|---|---|
| Cell ID | DQB1 Alleles | DQ54G-3 | DQ25-8 | DQ33 |
| TER145 | 05031/05031 | 34.9% | 34.1% | 39.5% |
| TER68 | 0201/05031 | 29.5% | 25.2% | 26.9% |
| TER74 | 0502/0601 | 0.0% | 28.4% | 27.1% |
| TER87 | 0201/0601 | 0.0% | 39.1% | 0.0% |
| TER123 | 0201/0501 | 0.0% | 0.0% | 28.9% |

Table 8 shows some data supporting an example in the DQB1 locus of the class II HLA genes. Again, a conventional probe, DQ25-8, binds with a relatively high signal to several DNA's—Ter145, Ter68, Ter74, and Ter87 corresponding to the presence of target sequences in alleles DQB1*05031 (homozygous), DQB1*05031 (heterozygous), DQB*0601, and DQB1*0601, respectively. DQ33, on the other hand, binds with a relatively high signal to DNA's Ter145, Ter68, Ter74, and Ter123 corresponding to the presence of target sequences in alleles DQB1*05031 (homozygous), DQB1*05031 (heterozygous), DQB1*0502, and DQB1*0501, respectively. As in previous examples, using the two conventional probes does not distinguish the trans configurations for recognitions sites as in Ter74 (DQB1*0502/DQB1*0601) from the cis configuration as in Ter145 or Ter68, both of which contain DQB1*05031. Gap probe DQ54G-3, which recognizes both target sequences, but only in the cis configuration, gives a relatively high signal only for DNA containing the DQB1*05031 allele. The positive control sequence for DQB1 locus Exon 2 is 5'-gTCCCgTTggTgAAgTAgCAC-3' (SEQ ID NO: 40) and 5'-gTCCCATTggTgAAgTAgCAC-3' (SEQ ID NO: 41).

Example 5

An example similar to Example 1 involving DRB1*0308 was performed using "half-probes," i.e. probes having shorter sequences identical to only one of the two probe regions for gap-probe OLR-4431-3. These "half-probes" (shown in Table 9) were compared to OLR-4431-3 for their binding to DRB1*0308, other DRB1*03 alleles, or DRB1*11 alleles for the samples tested. Table 9, below sets out the relationship between the sequences of these DRB1 alleles and the gap and half probes used in the experiment. The half-probes gave no or virtually no signal over background (always <1%) for DRB1*0308, other DRB1*03 alleles, or DRB1*11 alleles. OLR-4431-3 gave a high signal (64.0%) again only for DRB1*0308 DNA (table 10). This example demonstrates that the short, single site recognition sequences by themselves were incapable of stably binding to any of the DRB1* alleles in this experiment, but when put together as a single sequence were capable of binding to DRB1*0308. The individual half-probes have a binding capacity below threshold for this experiment for the recognition sequences found in the tested alleles. Combining the "half-probe" sequences generates a probe that has a binding capacity above the threshold only for the allele containing target regions for both "half-probes" or probe regions in the design of this experiment.

TABLE 9

Sequence Alignment of DRB1 Allele Target Sequences and Probes

| Sequence Type | Sequence Name(s) and Corresponding Relevant Sequence ID Numbers | Region 1 (Numbers in First Row Below Refer to Relevant Amino Acid Positions of Nucleotides in Subsequent Rows) | | | | | | | Inter-Region |
|---|---|---|---|---|---|---|---|---|---|
| | | 55 | 56 | 57 | 58 | 59 | 60 | 61 | |
| Reference Allele | DRB1*0101 (SEQ ID NOS: 1 and 2) | CGG | CCT | GAT | GCC | GAG | TAC | TGG | // |
| Alleles | DRB1*0308, DRB1*1107 (SEQ ID NOS: 3 and 4) | — | — | — | —AG | — | — | — | // |
| Probe | OLR4431-3 (SEQ ID NO: 7) | — | — | —AG | — | — | | | TTTT |
| Probe | OLR-4611 (SEQ ID NO: 42) | — | — | —AG | — | — | | | TTTT |
| Probe | OLR-4612 (SEQ ID NO: 43) | — | — | —AG | — | — | | | |
| Probe | OLR-4613 (SEQ ID NO: 44) | | | | | | | | |
| Probe | OLR-4614 (SEQ ID NO: 45) | | | | | | | | |

| Sequence Type | Sequence Name(s) and Corresponding Relevant Sequence ID Numbers | Region 2 (Numbers in First Row Below Refer to Relevant Amino Acid Positions of Nucleotides in Subsequent Rows) | | | | | | |
|---|---|---|---|---|---|---|---|---|
| | | 69 | 70 | 71 | 72 | 73 | 74 | 75 |
| Reference Allele | DRB1*0101 (SEQ ID NOS: 1 and 2) | GAG | CAG | AGG | CGG | GCC | GCG | GTG |
| Alleles | DRB1*0308, DRB1*1107 (SEQ ID NOS: 3 and 4) | — | — | —A— | — | —G— | CG— | — |
| Probe | OLR4431-3 (SEQ ID NO: 7) | — | — | —A— | — | —G | | |
| Probe | OLR-4611 (SEQ ID NO: 42) | | | | | | | |
| Probe | OLR-4612 (SEQ ID NO: 43) | | | | | | | |

TABLE 9-continued

Sequence Alignment of DRB1 Allele Target Sequences and Probes

| | | | | | | |
|---|---|---|---|---|---|---|
| Probe | OLR-4613 (SEQ ID NO: 44) | —— | —— | —A— | —— | —G |
| Probe | OLR-4614 (SEQ ID NO: 45) | —— | —— | —A— | —— | — |

TABLE 10

Fluorescent Signal Intensity of the Probes Compared to the Control Probe

| | | % (Test probe signal/Control probe signal) | | | | |
|---|---|---|---|---|---|---|
| Cell ID | DRB1 Alleles | OLR-4431-3 | OLR4611 | OLR4612 | OLR4613 | OLR4614 |
| GN090 | 0308, 0405 | 64.0% | 0.0% | 0.0% | 0.1% | 0.3% |
| TER227 | 03021, 03021 | 0.5% | 0.0% | 0.0% | 0.6% | 0.4% |
| TER87 | 0301, 0803 | 0.2% | 0.0% | 0.0% | 0.3% | 0.2% |
| TER118 | 0301, 1202 | 0.0% | 0.0% | 0.0% | 0.0% | 0.0% |
| TER119 | 0101, 1101 | 0.0% | 0.0% | 0.0% | 0.1% | 0.3% |
| TER156 | 1104, 1404 | 0.0% | 0.0% | 0.0% | 0.0% | 0.3% |

Table 10 showed gap-probe OLR4431-3 produce a relative high signal only to DNA from cell GN090 which containing DRB1*0308. OLR4611, OLR4612, OLR4613 and OLR4616 are probes with only one of the two gap regions in OLR4431-3. None of the probes produce any recognizable signal to any of the DNA samples. This example demonstrated that co-operative binding of the two probe regions is necessary in producing a positive signal to the desired target sequences. The positive control probe sequence for DRB1 Exon 2 is 5'-ggAACAgCCAgAAggAC-3' (seq id no: 46).

Example 6

In this example, the gap probe, OLR4029-6 recognizes two short target regions, a 15 base region (codons 12-16) near the 5' end of Exon 2 and a 12 base region (codons 68-71) nearer the 3' end of Exon 2 in the DRB1*16 group of alleles (table 11). The two recognized (target) regions are 150 bases apart. The DRB1*16 group is identical in sequence to the DRB1*15 group at the 5' end of Exon 2 (table 11). (The two groups are actually "splits" or subgroups of an originally designated group, DR2.) For typing purposes, it would be useful to be able to distinguish an allele in the DRB1*16 group from one in the DRB1*15 group using a single probe. Table 11, below sets out the relationship between the sequences of these DRB1 alleles and the gap probe used to detect them.

TABLE 11

Alignment of DRB1 Allele Target Sequences and Probes

| Sequence Type | Sequence Name(s) and Corresponding Relevant Sequence ID Numbers | Region 1 (Numbers in First Row Below Refer to Relevant Amino Acid Positions of Nucleotides in Subsequent Rows) | | | | | | | | |
|---|---|---|---|---|---|---|---|---|---|---|
| | | 8 | 9 | 10 | 11 | 12 | 13 | 14 | 15 | 16 |
| Reference Allele | DRB1*0101 (SEQ ID NOS: 47 and 48) | TTG | TGG | CAG | CTT | AAG | TTT | GAA | TGT | CAT |
| Allele | DRB1*1501 (SEQ ID NOS: 49 and 50) | C— | —— | —— | —C— | —— | AGG | —G | —— | —— |
| Allele | DRB1*1502 (SEQ ID NOS: 49 and 50) | C— | —— | —— | —C— | —— | AGG | —G | —— | —— |
| Allele | DRB1*16011 (SEQ ID NOS: 49 and 51) | C— | —— | —— | —C— | —— | AGG | —G | —— | —— |
| Allele | DRB1*16021 (SEQ ID NOS: 49 and 52) | C— | —— | —— | —C— | —— | AGG | —G | —— | —— |
| Probe | OLR-4029-6 (SEQ ID NO: 53) | | | | —C— | —— | AGG | —G | —— | |

| Sequence Type | Sequence Name(s) and Corresponding Relevant Sequence ID Numbers | Inter-Region | Region 2 (Numbers in First Row Below Refer to Relevant Amino Acid Positions of Nucleotides in Subsequent Rows) | | | | | | |
|---|---|---|---|---|---|---|---|---|---|
| | | | 67 | 68 | 69 | 70 | 71 | 72 | 73 |
| Reference Allele | DRB1*0101 (SEQ ID NOS: 47 and 48) | // | CTC | CTG | GAG | CAG | AGG | CGG | GCC |
| Allele | DRB1*1501 (SEQ ID NOS: 49 and 50) | // | A— | —— | —— | —— | GC— | —— | —— |
| Allele | DRB1*1502 (SEQ ID NOS: 49 and 50) | // | A— | —— | —— | —— | GC— | —— | —— |
| Allele | DRB1*16011 (SEQ ID NOS: 49 and 51) | // | T— | —— | —A | G—C | —— | —C | —— |

TABLE 11-continued

Alignment of DRB1 Allele Target Sequences and Probes

| Allele | DRB1*16021 (SEQ ID NOS: 49 and 52) | // | — | — | —A | G—C | — | —C | — |
|---|---|---|---|---|---|---|---|---|---|
| Probe | OLR-4029-6 (SEQ ID NO: 53) | | | — | —A | G—C | — | | |

TABLE 12

Signal Intensity of the Probes Compared to the Control Probe

| CELL ID | DRB1* GENOTYPE | 4029-6 SIGNAL |
|---|---|---|
| TER69 | 09012/1502 | 7.8% |
| E18994 | 07011/1501 | 8.9% |
| E10351 | 1303/16011 | 29.4% |
| TER262 | 1413/16021 | 22.8% |
| TER85 | 0801/1401 | 0.0% |
| Hicks | 0804/1101 | 0.1% |
| TER160 | 0415/1301 | 0.0% |
| AP630 | 03021/1201 | 0.0% |

Probe OLR4029-6 does indeed show a significant signal to distinguish DRB1*16 alleles from DRB1*15. The signal for a DRB1*16 allele is 2.5 times that of a DRB1*15 allele in this experiment even with a gap of 150 bases between the two target regions (table 12). The DR2-specific sequence at the 5'-end identifies the allele as DRB1*15 or DRB1*16, but is insufficient to yield a large signal (table 12). The DRB1*16-specific sequence acts in concert with the 5' DR2-specific signal to significantly raise the signal for DRB1*16 alleles (table 12). The 3' probe region is insufficient by itself to give a signal above background for DNAs containing the short target sequence at codons 68-11 in alleles DRB1*0801, DRB1*0804, DRB1*1101, DRB1*0415, and DRB1*1201 represented in this experiment. The positive control probe sequence for DRB1 Exon 2 is 5'-ggAACAgCCAgAAggAC-3' (SEQ ID NO: 9).

What is claimed is:

1. A method for detecting the presence of a target nucleic acid sequence on a nucleic acid strand having a first target nucleic acid sequence and a second target nucleic acid sequence and distinguishing the target from an allelic variant thereof comprising the steps of:
performing nucleic acid amplification on a sample suspected of containing said target nucleic acid sequence to produce an amplification mixture suspected of containing amplified target nucleic acid sequence;
denaturing and neutralizing the amplification mixture suspected of containing said amplified target nucleic acid sequence;
contacting the denatured and neutralized amplification mixture suspected of containing said amplified target nucleic acid sequence with a single probe under hybridizing conditions;
wherein the nucleotide sequence of said single probe comprises (1) a first probe region at its 5'-end that is substantially complementary to a first target region characteristic of said target nucleic acid sequence, and (2) a second probe region, located 3' to said first probe region, where the second probe region is substantially complementary to a second target region characteristic of said target nucleic acid sequence on the target nucleic acid strand wherein when said first target region is contiguous with said second target region on the target nucleic acid strand then the first and second probe regions on the probe are separated by a spacer region of nucleic acid, and further wherein when the first and second probe regions on the probe are contiguous then there exists an intervening sequence between the first and second target regions on the target nucleic acid strand;
whereby for said selected hybridization conditions the first and second probe regions are such that the probe is stably hybridized to the target nucleic acid strand to form a detectable probe: target hybrid only when the first probe region is substantially complementary to the first target region and the second probe region is substantially complementary to the second target region,
but wherein for said selected hybridization conditions the probe is not stably hybridized to the target nucleic acid strand to form a probe:target hybrid detectable above a threshold indicative of stable hybridization when either the first probe region is not substantially complementary to the first target region or the second probe region is not substantially complementary to the second target region;
wherein said first and second probe regions on the probe are separated by a spacer region of nucleic acid sequence that is not complementary to the sequence of the sample nucleic acid strand between the first and second target regions on said target nucleic acid and wherein there exists an intervening sequence between the first and second target regions on said target nucleic acid that is not complementary to the sequence of the sample nucleic acid strand between the first and second probe regions on the probe;
separating the probe from the target nucleic acid when either the first probe region is not substantially complementary to the first target region or the second probe region is not substantially complementary to the second target region; and
detecting the presence or absence of the stable probe: target hybrid in the absence of elongation of the probe: target hybrid and in the absence of nicking either the probe or target as an indication of the presence of the target nucleic acid sequence in the sample,
wherein no more than two (2) mismatches relative to the complementary sequence are present in either or both of the first and second target regions respectively.

2. The method of claim 1 wherein said spacer is from 1 to 30 bases long.

3. The method of claim 1 wherein said spacer is from 3 to 10 bases long.

4. The method of claim 1 wherein said first target region is from 1 to 350 bases from said second target region on the target nucleic acid sequence.

5. The method of claim 1 wherein the target nucleic acid sequence is characteristic of one or more human leukocyte antigens (HLA) or T-cell receptor (TCR) gene sequences.

6. The method of claim 1 wherein the sample suspected of containing said target nucleic acid is derived from a human being.

7. The method of claim 1 wherein the first and second probe regions, or first or second probe regions, each comprise no more than one (1) mismatch relative to the complementary sequence in the first and second target regions respectively.

8. A method for detecting the presence of a target nucleic acid sequence on a nucleic acid strand having a first target nucleic acid sequence and a second target nucleic acid sequence and distinguishing the target from an allelic variant thereof comprising the steps of:
contacting a denatured and neutralized nucleic acid amplification mixture suspected of containing target nucleic acid sequence with a single probe under hybridizing conditions;
wherein the nucleotide sequence of said single probe comprises (1) a first probe region at its 5'-end that is substantially complementary to a first target region characteristic of said target nucleic acid sequence, and (2) a second probe region, located 3' to said first probe region, where the second probe region is substantially complementary to a second target region characteristic of said target nucleic acid sequence on the target nucleic acid strand wherein when said first target region is contiguous with said second target region on the target nucleic acid strand then the first and second probe regions on the probe are separated by a spacer region of nucleic acid, and further wherein when the first and second probe regions on the probe are contiguous then there exists an intervening sequence between the first and second target regions on the target nucleic acid strand;
whereby for said selected hybridization conditions the first and second probe regions are such that the probe is stably hybridized to the target nucleic acid strand to form a detectable probe: target hybrid only when the first probe region is substantially complementary to the first target region and the second probe region is substantially complementary to the second target region,
but wherein for said selected hybridization conditions the probe is not stably hybridized to the target nucleic acid strand to form a probe:target hybrid detectable above a threshold indicative of stable hybridization when either the first probe region is not substantially complementary to the first target region or the second probe region is not substantially complementary to the second target region;

wherein said first and second probe regions on the probe are separated by a spacer region of nucleic acid sequence that is not complementary to the sequence of the sample nucleic acid strand between the first and second target regions on said target nucleic acid and wherein there exists an intervening sequence between the first and second target regions on said target nucleic acid that is not complementary to the sequence of the sample nucleic acid strand between the first and second probe regions on the probe;

separating the probe from the target nucleic acid when either the first probe region is not substantially complementary to the first target region or the second probe region is not substantially complementary to the second target region; and detecting the presence or absence of the stable probe:target hybrid in the absence of elongation of the probe:target hybrid and in the absence of nicking either the probe or target as an indication of the presence of the target nucleic acid sequence in the sample, wherein no more than two (2) mismatches relative to the complementary sequence are present in each of the first and second target regions respectively.

9. The method of claim 8 wherein said spacer is from 1 to 30 bases long.

10. The method of claim 8 wherein said spacer is from 3 to 10 bases long.

11. The method of claim 8 wherein said first target region is from 1 to 350 bases from said second target region on the target nucleic acid sequence.

12. The method of claim 8 wherein the target nucleic acid sequence is characteristic of one or more human leukocyte antigens (HLA) or T-cell receptor (TCR) gene sequences.

13. The method of claim 8 wherein the sample suspected of containing said target nucleic acid is derived from a human being.

14. The method of claim 8 wherein the first and second probe regions, or first or second probe regions, each comprise no more than one (1) mismatch relative to the complementary sequence in the first and second target regions respectively.

* * * * *